(12) United States Patent
Allen, IV et al.

(10) Patent No.: US 9,956,030 B2
(45) Date of Patent: *May 1, 2018

(54) ELECTROSURGICAL FORCEPS WITH STAMPED DOUBLE-FLANGE JAWS AND U-SHAPED DRIVE ACTUATION MECHANISM

(71) Applicant: COVIDIEN LP, Mansfield, MA (US)

(72) Inventors: James D. Allen, IV, Broomfield, CO (US); Edward M. Chojin, Boulder, CO (US); Joseph D. Bucciaglia, Louisville, CO (US)

(73) Assignee: Covidien LP, Mansfield, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/182,047

(22) Filed: Jun. 14, 2016

(65) Prior Publication Data

US 2016/0287318 A1    Oct. 6, 2016

Related U.S. Application Data

(63) Continuation of application No. 14/604,385, filed on Jan. 23, 2015, now Pat. No. 9,375,263, which is a
(Continued)

(51) Int. Cl.
*A61B 18/14* (2006.01)
*A61B 17/29* (2006.01)
(Continued)

(52) U.S. Cl.
CPC .......... *A61B 18/1445* (2013.01); *A61B 17/29* (2013.01); *A61B 2017/00367* (2013.01);
(Continued)

(58) Field of Classification Search
None
See application file for complete search history.

(56) References Cited

U.S. PATENT DOCUMENTS

| 702,472 A | 6/1902 | Pignolet |
| 2,801,633 A | 8/1957 | Ehrlich |

(Continued)

FOREIGN PATENT DOCUMENTS

| CN | 100493469 C | 6/2009 |
| CN | 101516285 A | 8/2009 |

(Continued)

OTHER PUBLICATIONS

Peterson et al. "Comparison of Healing Process Following Ligation with Sutures and Bipolar Vessel Sealing" Surgical Technology International (2001).

(Continued)

*Primary Examiner* — Kennedy Schaetzle

(57) ABSTRACT

A surgical instrument includes a housing that supports an elongated shaft. A selectively movable drive rod extends through the elongated shaft and carries a cam pin in a longitudinal direction. An end effector for surgically treating tissue is supported by the elongated shaft and includes upper and lower jaw members pivotally coupled to one another about a pivot axis. The upper jaw member includes a first pair of laterally spaced flanges, and the lower jaw member includes a second pair of laterally spaced flanges defining a camming slot for engaging the cam pin. The flanges are arranged in an offset configuration where one flange of the upper jaw member is positioned on a laterally exterior side of a corresponding flange of the lower jaw member, and the other flange of the upper jaw member is positioned on a laterally interior side of the other flange of the lower jaw member.

13 Claims, 23 Drawing Sheets

Related U.S. Application Data continuation of application No. 13/461,378, filed on May 1, 2012, now Pat. No. 8,968,311.

(51) Int. Cl.
*A61B 17/00* (2006.01)
*A61B 18/00* (2006.01)

(52) U.S. Cl.
CPC ............ *A61B 2017/2936* (2013.01); *A61B 2018/0063* (2013.01); *A61B 2018/00607* (2013.01); *A61B 2018/1455* (2013.01); *F04C 2270/0421* (2013.01)

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| 4,793,218 A | 12/1988 | Jordan et al. |
| D299,413 S | 1/1989 | DeCarolis |
| 5,100,506 A | 3/1992 | Sturtevant et al. |
| 5,242,456 A | 9/1993 | Nash et al. |
| D343,453 S | 1/1994 | Noda |
| 5,302,234 A | 4/1994 | Grace et al. |
| 5,317,938 A | 6/1994 | de Juan, Jr. et al. |
| D348,930 S | 7/1994 | Olson |
| D349,341 S | 8/1994 | Lichtman et al. |
| D354,564 S | 1/1995 | Medema |
| 5,383,471 A | 1/1995 | Funnell |
| 5,395,364 A | 3/1995 | Anderhub et al. |
| D358,887 S | 5/1995 | Feinberg |
| 5,431,667 A | 7/1995 | Thompson et al. |
| 5,486,185 A | 1/1996 | Freitas et al. |
| 5,486,189 A | 1/1996 | Mudry et al. |
| 5,522,830 A | 6/1996 | Aranyi |
| 5,522,839 A | 6/1996 | Pilling |
| 5,539,973 A | 7/1996 | Smith et al. |
| 5,571,129 A | 11/1996 | Porter |
| 5,620,447 A | 4/1997 | Smith et al. |
| 5,626,609 A | 5/1997 | Zvenyatsky et al. |
| D384,413 S | 9/1997 | Zlock et al. |
| 5,707,392 A | 1/1998 | Kortenbach |
| 5,716,374 A | 2/1998 | Francese et al. |
| H1745 H | 8/1998 | Paraschac |
| 5,833,692 A | 11/1998 | Cesarini et al. |
| D402,028 S | 12/1998 | Grimm et al. |
| D408,018 S | 4/1999 | McNaughton |
| D416,089 S | 11/1999 | Barton et al. |
| 6,013,028 A | 1/2000 | Jho et al. |
| D424,694 S | 5/2000 | Tetzlaff et al. |
| D425,201 S | 5/2000 | Tetzlaff et al. |
| 6,117,158 A | 9/2000 | Measamer et al. |
| H1904 H | 10/2000 | Yates et al. |
| 6,202,465 B1 | 3/2001 | Jankoski et al. |
| 6,277,117 B1 | 8/2001 | Tetzlaff et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,101,371 B2 | 9/2006 | Dycus et al. |
| D531,311 S | 10/2006 | Guerra et al. |
| 7,122,035 B2 | 10/2006 | Canady |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| 7,186,261 B2 | 3/2007 | Prestel |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,267,677 B2 | 9/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,685,056 B2* | 4/2014 | Evans ............... A61B 17/29 606/205 |
| 8,968,311 B2* | 3/2015 | Allen, IV ........... A61B 18/1445 606/45 |
| 9,060,780 B2* | 6/2015 | Twomey ............ A61B 18/1445 |
| 9,375,263 B2* | 6/2016 | Allen, IV ........... A61B 18/1445 |
| 2002/0058925 A1 | 5/2002 | Kaplan et al. |
| 2002/0161364 A1 | 10/2002 | Mulier et al. |
| 2004/0148992 A1 | 8/2004 | Huang |
| 2004/0193153 A1* | 9/2004 | Sartor ............... A61B 18/1445 606/48 |
| 2005/0090837 A1* | 4/2005 | Sixto, Jr. ............ A61B 17/1285 606/139 |
| 2005/0240218 A1 | 10/2005 | Freed et al. |
| 2006/0052777 A1* | 3/2006 | Dumbauld ............ A61B 17/29 606/51 |
| 2008/0083257 A1 | 4/2008 | Taylor et al. |
| 2008/0264139 A1 | 10/2008 | Rosenbohm et al. |
| 2008/0319467 A1 | 12/2008 | Wenchell |
| 2009/0088743 A1 | 4/2009 | Masuda |
| 2009/0182327 A1* | 7/2009 | Unger ............... A61B 18/1445 606/46 |
| 2010/0145334 A1 | 6/2010 | Olson et al. |
| 2011/0009864 A1 | 1/2011 | Bucciaglia et al. |
| 2011/0144665 A1 | 6/2011 | Malkowski |

FOREIGN PATENT DOCUMENTS

| | | |
|---|---|---|
| CN | 201299462 Y | 9/2009 |
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3712328 U1 | 2/1988 |
| DE | 04303882 A1 | 8/1994 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |

(56) References Cited

FOREIGN PATENT DOCUMENTS

| | | |
|---|---|---|
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102008018406 B3 | 7/2009 |
| EP | 0584787 A1 | 3/1994 |
| EP | 1159926 A2 | 12/2001 |
| EP | 1810625 A1 | 7/2007 |
| EP | 2347725 A1 | 7/2011 |
| EP | 2399538 A2 | 12/2011 |
| EP | 2574299 A2 | 4/2013 |
| JP | 61-501068 | 9/1984 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 08056955 | 3/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 09010223 | 1/1997 |
| JP | 9-122138 A | 5/1997 |
| JP | 0010000195 A | 1/1998 |
| JP | H10-24051 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 2001-8944 | 1/2001 |
| JP | 2001029356 A | 2/2001 |
| JP | 2001128990 A | 5/2001 |
| JP | 2001190564 A | 7/2001 |
| JP | 2001-003400 | 11/2001 |
| JP | 2002136525 A | 5/2002 |
| JP | 2002528166 A | 9/2002 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2005110264 A3 | 4/2006 |
| WO | 2010014825 A1 | 2/2010 |

OTHER PUBLICATIONS

"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Surdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 39, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012 James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2013, Joseph D. Bucciaglia.
U.S. Appl. No. 13/584,194, filed Aug. 13, 2012, Sean T. Dycus.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.

(56) References Cited

OTHER PUBLICATIONS

Tinkcler L.F., "Combined Diathermy and Suction Forceps", Feb. 6, 1967, British Medical Journal Feb. 6, 1976, vol. 1, No. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Chinese First Office Action, and English Language translation, from Chinese Appl. No. 201310154366.X dated Feb. 1, 2016.
Australian Patent Examination Report No. 1 from Appl. No. AU 2015203497 issued Mar. 16, 2016.
Japanese Office Action with English language translation issued in JP Appl. No. 2013-094330 mailed Aug. 25, 2016.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 168419.7 dated Oct. 20, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report No. 13166213.2 dated Nov. 25, 2013.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.

(56) References Cited

OTHER PUBLICATIONS

U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
Extended European Search Report dated May 28, 2015 in Application No. EP 15151110.2.
Int'l Search Report EP 08 004655.0 dated Jun. 24, 2008.
Int'l Search Report EP 08 006732.5 dated Jul. 29, 2008.
Extended European Search Report from Appl. No. EP 16196552.0 dated Feb. 27, 2017.
Examiner's First Report issued in Appl. No. AU 2016219736 dated Sep. 27, 2017.
Japnese Office Action, and English language translation, issued in Appl. No. JP 2016-227660, dated Sep. 25, 2017 (7 pages).

\* cited by examiner

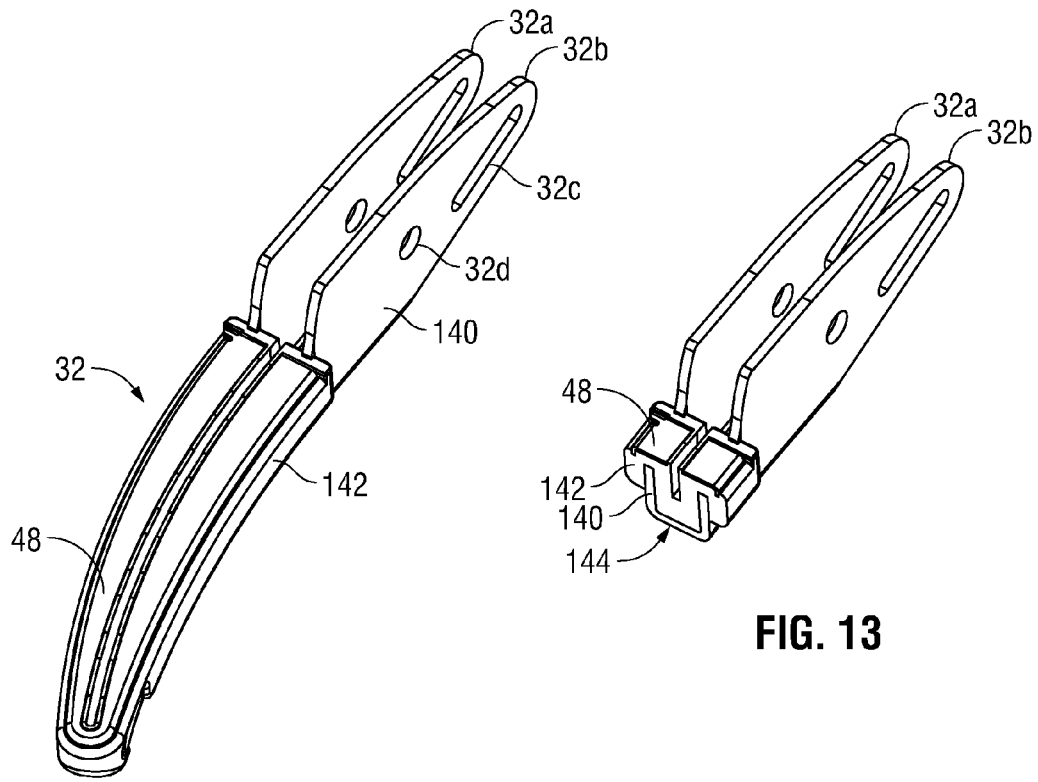
FIG. 12
FIG. 13
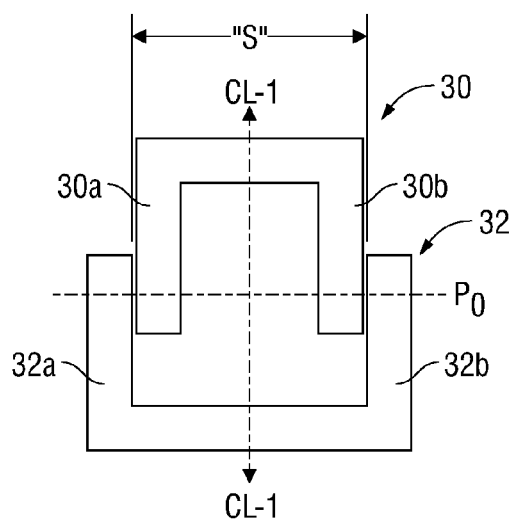
FIG. 14
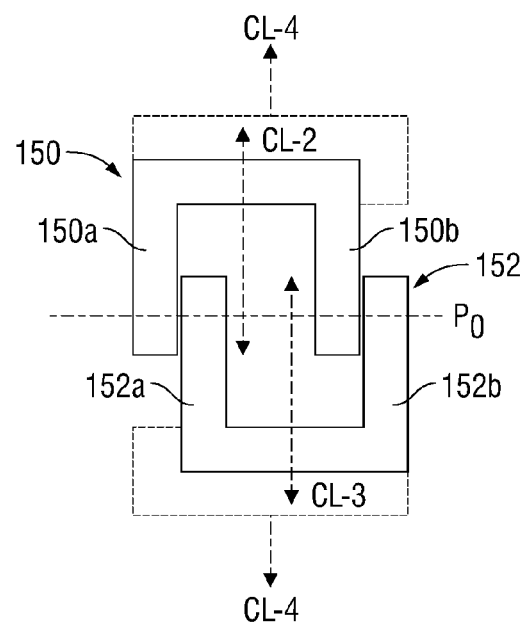
FIG. 15

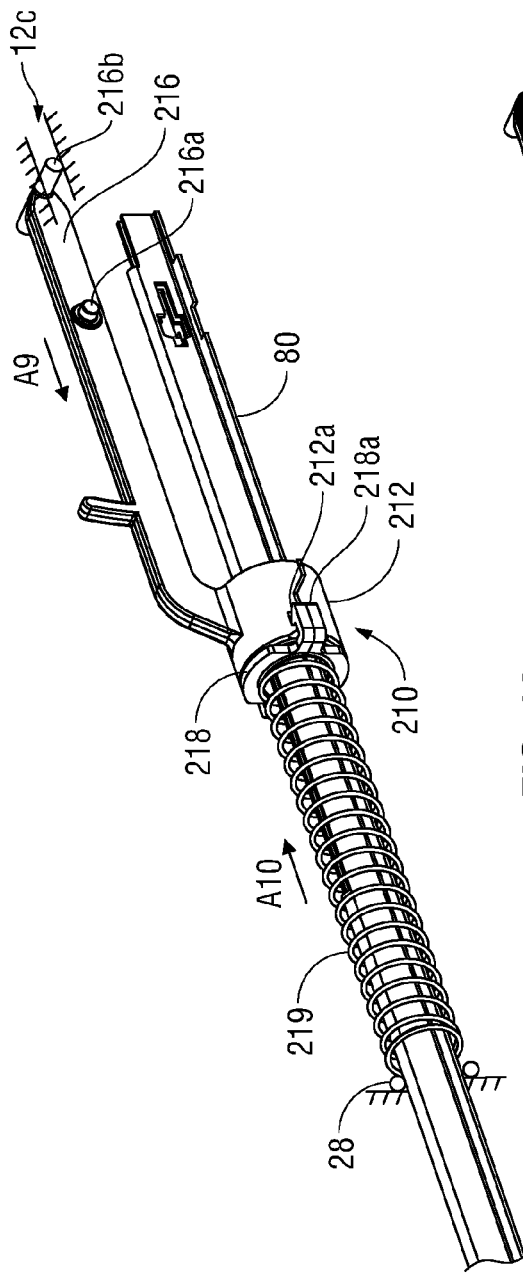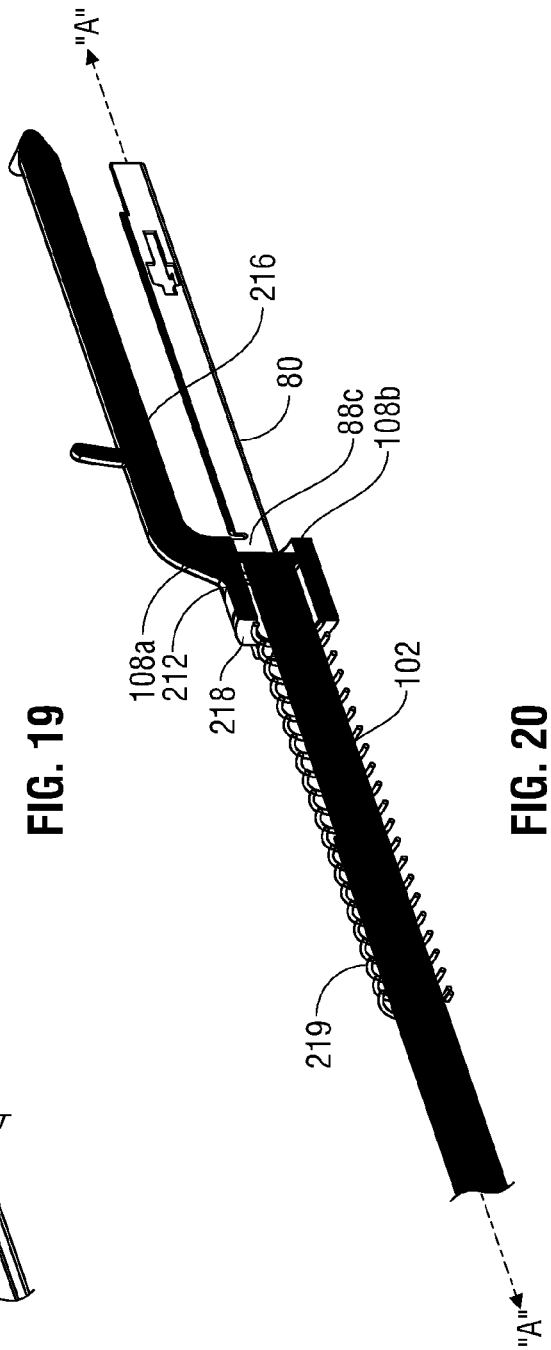
FIG. 19
FIG. 20

ELECTROSURGICAL FORCEPS WITH STAMPED DOUBLE-FLANGE JAWS AND U-SHAPED DRIVE ACTUATION MECHANISM

CROSS-REFERENCE TO RELATED APPLICATIONS

This application is a continuation of U.S. patent application Ser. No. 14/604,385 filed on Jan. 23, 2015, now U.S. Pat. No. 9,375,263, which is a continuation of U.S. patent application Ser. No. 13/461,378 filed on May 1, 2012, now U.S. Pat. No. 8,968,311, the entire contents of each of which are incorporated herein by reference.

BACKGROUND

1. Technical Field

The present disclosure relates generally to the field of surgical instruments. In particular, the disclosure relates to an endoscopic electrosurgical forceps that is economical to manufacture and is capable of sealing and cutting relatively large tissue structures.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm2 to about 16 kg/cm2.

SUMMARY

The present disclosure describes a surgical instrument for treating tissue that is economical to manufacture and is capable of sealing and cutting relatively large tissue structures. The surgical instrument includes a housing and an elongated shaft extending distally therefrom. The elongated shaft includes a proximal portion coupled to the housing and a distal portion opposite the proximal portion, and defines a longitudinal axis. A drive rod extends at least partially through the elongated shaft, and is selectively movable in a longitudinal direction with respect to the elongated shaft. A cam pin is supported by the drive rod such that longitudinal movement of the drive rod is imparted to the cam pin. An end effector is supported by the distal portion of the elongated shaft, and is adapted for treating tissue. The end effector includes an upper jaw member pivotally coupled to the distal portion of the elongated shaft about a pivot axis, and the upper jaw member includes a first pair of laterally spaced flanges each defining a camming slot for engaging the cam pin. The end effector also includes a lower jaw member pivotally coupled to the distal portion of the elongated shaft about the pivot axis, and the lower jaw member includes a second pair of laterally spaced flanges each defining a camming slot for engaging the cam pin. The first and second pairs of flanges of the jaw members are arranged in an offset configuration such that one flange of the upper jaw member is positioned on a laterally exterior side of a corresponding flange of the lower jaw member, and the other flange of the upper jaw member is positioned on a laterally interior side of the other flange of the lower jaw member.

The upper and lower jaw members may be constructed as substantially identical components positioned in a laterally offset manner with respect to one another. Each of the flanges may extend proximally from a tissue engaging portion of the jaw members, and the tissue engaging portions may be substantially curved. The pivot axis may extends through each of the flanges in a direction substantially transverse to the longitudinal axis.

The drive rod may extend through the jaw members on a laterally interior side of each of the flanges, and the drive rod may exhibit a generally u-shaped profile. The surgical instrument may further include a knife selectively movable in a longitudinal direction with respect to the drive rod, and the knife may be supported within the u-shaped profile such that the drive rod provides restricts lateral movement of the knife in a first lateral plane. The drive rod may also include an overfold disposed opposite a u-shaped connector portion of the drive rod such that the knife is substantially surrounded on four lateral sides, and such that the overfold and the u-shaped connector portion restrict movement of the knife in a second lateral plane that is orthogonal to the first lateral plane.

The jaw member may be adapted for electrosurgically treating tissue and may include electrical wires extending proximally therefrom for facilitating connection of the respective jaw members to a source of electrosurgical energy. At least one of the flanges of each of the jaw members may include an electrically isolative wire guide disposed on a lateral side thereof, wherein the electrical wire of the respective jaw member extends through the wire guide. The wire guides may be constructed of an electrically isolative plastic molded onto the respective flanges.

According to another aspect of the disclosure a surgical instrument includes a housing and an elongated shaft extending therefrom. The elongated shaft includes a proximal portion coupled to the housing and a distal portion opposite the proximal portion and defining a longitudinal axis. An end effector is supported by the distal portion of the elongated shaft. The end effector is adapted for treating tissue and includes first and second jaw members pivotally coupled to one another to move between open and closed configurations. Each of the jaw members includes a pair of laterally spaced flanges, and each of the flanges includes a camming surface thereon. A knife extends at least partially through the elongated shaft and is selectively movable in a longitudinal direction between the flanges of the jaw members. A blade of the knife is extendable into a tissue contacting portion of the jaw members. A drive rod extends at least partially through the elongated shaft and is selectively movable in a longitudinal direction with respect to the knife and with respect to the elongated shaft in response to manipulation of the housing. The drive rod carries a cam pin positioned to engage the camming surface of each of the flanges to induce the jaw members to move between the open and closed configurations. The drive rod substantially surrounds the knife on four lateral sides to restrict motion of the knife in at least two orthogonal planes.

The laterally spaced flanges of the jaw members may be arranged in a nestled configuration wherein both of the flanges of one of the jaw members are arranged within a laterally interior side of the laterally spaced flanges of the other of the jaw members. The knife may be constructed of a substantially flat piece of metal, and the drive rod may be constructed of metal folded to exhibit a generally u-shaped profile extending around the four lateral sides of the knife. A distal-most end of the drive rod may extend around the four lateral sides of the knife and a proximal portion of the drive rod may extend around fewer than four lateral sides of the knife.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 12 is a perspective view of a lower jaw member of the end effector of FIG. 1 depicting a double flange at a proximal end thereof;

FIG. 13 cross-sectional, perspective view of the lower jaw member of FIG. 12;

FIG. 14 is a schematic view of the nestled arrangement of the double flange of FIG. 12 with a double flange of an upper jaw member;

FIG. 15 is a schematic view of an alternative offset arrangement of double flanges of an alternate pair of jaw members;

FIG. 19 is a perspective view of a proximal portion of the knife actuation mechanism of FIG. 11; and FIG. 20 is a cross-sectional, perspective view of the knife actuation mechanism of FIG. 19.

DETAILED DESCRIPTION

The present disclosure relates to an electrosurgical apparatus and methods for performing electrosurgical procedures. More particularly, the present disclosure relates to electrosurgically sealing tissue. As is traditional, the term "distal" refers herein to an end of the apparatus that is farther from an operator, and the term "proximal" refers herein to the end of the forceps 10 which is closer to the operator.

Figure 1:
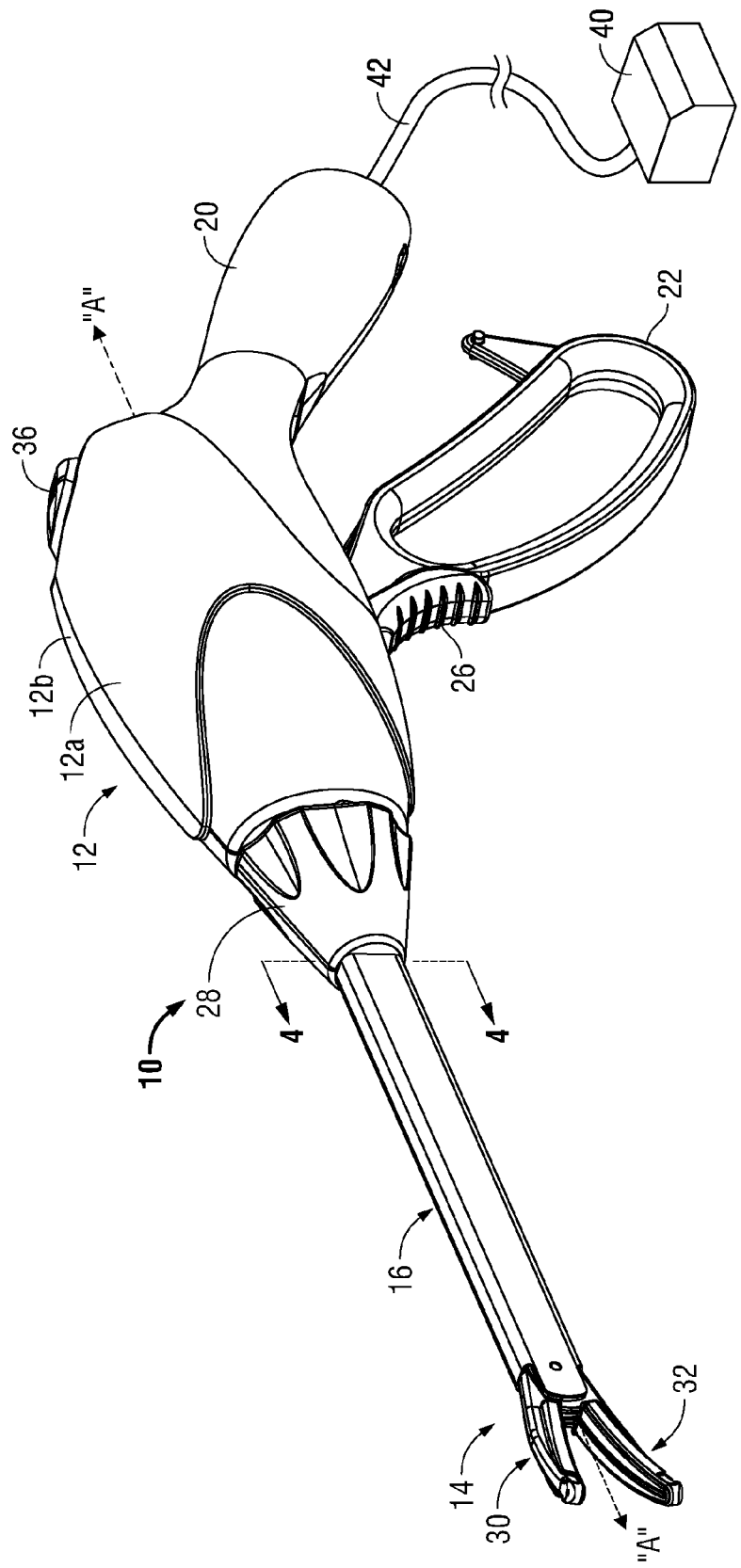
FIG. 1 is a perspective view of an electrosurgical forceps according to an embodiment of the present disclosure including a housing, an elongated shaft, and an end effector.

Referring initially to FIG. 1, an embodiment of an electrosurgical forceps 10 generally includes a housing 12 that supports various actuators thereon for remotely controlling an end effector 14 through an elongated shaft 16. Although this configuration is typically associated with instruments for use in laparoscopic or endoscopic surgical procedures, various aspects of the present disclosure may be practiced with traditional open instruments and in connection with endoluminal procedures as well.

The housing 12 is constructed of a left housing half 12a and a right housing half 12b. The left and right designation of the housing halves 12a, 12b refer to the respective directions as perceived by an operator using the forceps 10. The housing halves 12a, 12b may be constructed of sturdy plastic, and may be joined to one another by adhesives, ultrasonic welding or other suitable assembly methods.

To mechanically control the end effector 14, the housing 12 supports a stationary handle 20, a movable handle 22, a trigger 26 and rotation knob 28. The movable handle 22 is operable to move the end effector 14 between an open configuration (FIG. 2A) wherein a pair of opposed jaw members 30, 32 are disposed in spaced relation relative to one another, and a closed or clamping configuration (FIG. 2B) wherein the jaw members 30, 32 are closer together. Approximation of the movable handle 22 with the stationary handle 20 serves to move the end effector 14 to the closed configuration and separation of the movable handle 22 from the stationary handle 20 serves to move the end effector 14 open configuration. The trigger 26 is operable to extend and retract a knife blade 56 (see FIG. 2A) through the end effector 14 when the end effector 14 is in the closed configuration. The rotation knob 28 serves to rotate the elongated shaft 16 and the end effector 14 about a longitudinal axis A-A extending through the forceps.

To electrically control the end effector 14, the housing 12 supports a switch 36 thereon, which is operable by the user to initiate and terminate the delivery of electrosurgical energy to the end effector 14. The switch 36 is in electrical communication with a source of electrosurgical energy such as electrosurgical generator 40. The generator 40 may include devices such as the LIGASURE® Vessel Sealing Generator and the Force Triad® Generator as sold by Covidien. A cable 42 extends between the housing 12 and the generator 40 and may include a connector (not shown) thereon such that the forceps 10 may be selectively coupled and decoupled electrically from the generator 40. In other embodiments (not shown) a battery powered instrument may be provided in which a generator and connector may be internal or integral to the instrument.

Figure 2A:
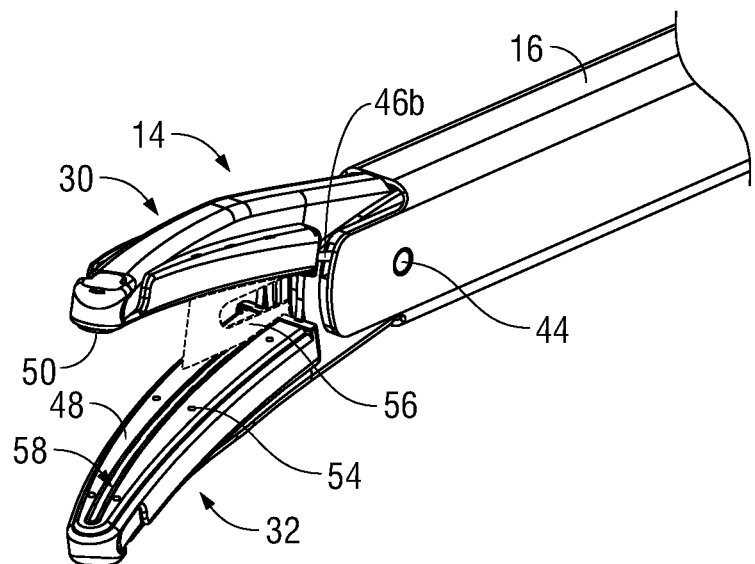
FIG. 2A is an enlarged perspective view of the end effector of FIG. 1 depicted with a pair of jaw members in an open configuration.
Figure 2B:
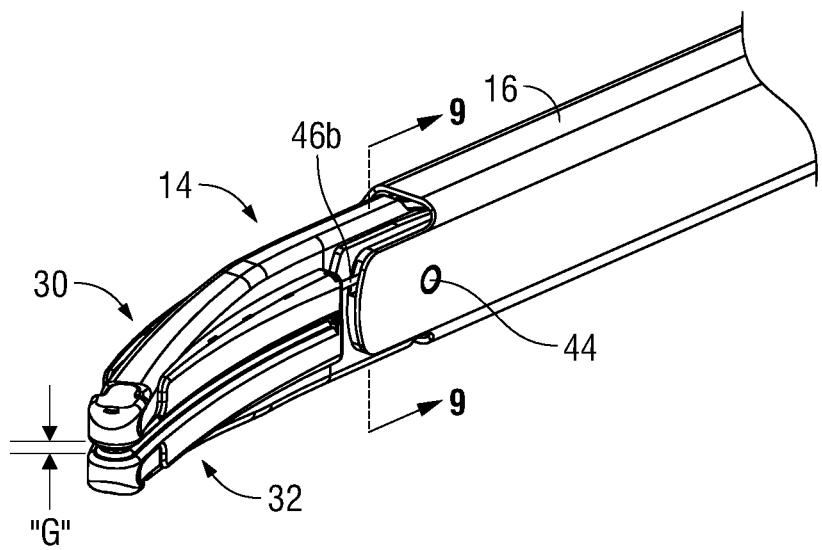
FIG. 2B is an enlarged perspective view of the end effector of FIG. 1 depicted with the pair of jaw members in a closed configuration.

Referring now to FIGS. 2A and 2B, the end effector 14 may be moved from the open configuration (FIG. 2A) wherein tissue (not shown) may be received between the jaw members 30, 32, and the closed configuration (FIG. 2B), wherein the tissue may be clamped and sealed. Upper jaw member 30 and lower jaw member 32 are mechanically coupled to the elongated shaft 16 about a pivot pin 44. The upper jaw member 30 is electrically coupled to cable 42, and thus to the generator 40, (see FIG. 1) through a wire 46b extending through the elongated shaft 16. The lower jaw member 32 is also coupled to the generator 40 by another wire 46a (FIG. 4) extending through the elongated shaft 16. The wires 46a, 46b provide an electrical pathway to a pair of electrically conductive, tissue-engaging sealing plates 48, 50 disposed on the lower and upper jaw members 32, 30, respectively. The sealing plate 48 of the lower jaw member 32 opposes a sealing plate 50 of the upper jaw member 30, and, in some embodiments, the sealing plates 48 and 50 are electrically coupled to opposite terminals, e.g., positive or active (+) and negative or return (−) terminals associated with the generator 40. Thus, bipolar energy may be provided through the end effector 14. Alternatively, the end effector 14 may be configured for delivering monopolar energy to the tissue. In a monopolar configuration, the end effector 14 delivers electrosurgical energy from an active terminal, e.g. (+), while a return pad (not shown) is placed generally on a patient and provides a return path to the opposite terminal, e.g. (−), of the generator 40.

The jaw members 30, 32 may be pivoted about the pivot pin 44 to move the end effector 14 to the closed configuration of FIG. 2B wherein the sealing plates 48, 50 provide a pressure to the tissue grasped therebetween. In some embodiments, to provide an effective seal, a pressure within a range between about 3 kg/cm2 to about 16 kg/cm2 and, desirably, within a working range of 7 kg/cm2 to 13 kg/cm2 may be applied to the tissue. Also, in the closed configuration, a separation or gap distance "G" may be maintained between the sealing plates 48, 50 by an array of stop members 54 disposed on or adjacent the sealing plates 48, 50. The stop members 54 contact opposing surfaces on the opposing jaw member 30, 32 and prohibit further approximation of the sealing plates 48, 50. In some embodiments, to provide an effective tissue seal, an appropriate gap distance of about 0.001 inches to about 0.006 inches and, desirably, between about 0.002 and about 0.005 inches may be provided. In some embodiments, the stop members 54 are constructed of an electrically non-conductive plastic or other material molded onto the jaw members 30, 32, e.g., by a process such as overmolding or injection molding. In other embodiments, the stop members 54 are constructed of a heat-resistant ceramic deposited onto the jaw members 30, 32. Other methods of controlling gap are contemplated including those described in commonly assigned patent application Ser. No. 13/835,004 filed Mar. 15, 2013 entitled "Gap Control Via Overmold Teeth and Hard Stops" (now U.S. Pat. No. 8,939,975).

Electrosurgical energy may be delivered to the tissue through the electrically conductive seal plates 48, 50 to effect a tissue seal. Once a tissue seal is established, a knife blade 56 may be advanced through a knife channel 58 defined in the jaw members 30, 32 to transect the sealed tissue. Knife blade 56 is depicted in FIG. 2A as extending from the elongated shaft 16 when the end effector 14 is in an open configuration. In some embodiments, a knife lockout is provided to prevent extension of the knife blade 56 into the knife channel 58 when the end effector 14 is in the open configuration, thus preventing accidental or premature transection of tissue.

Figure 3:
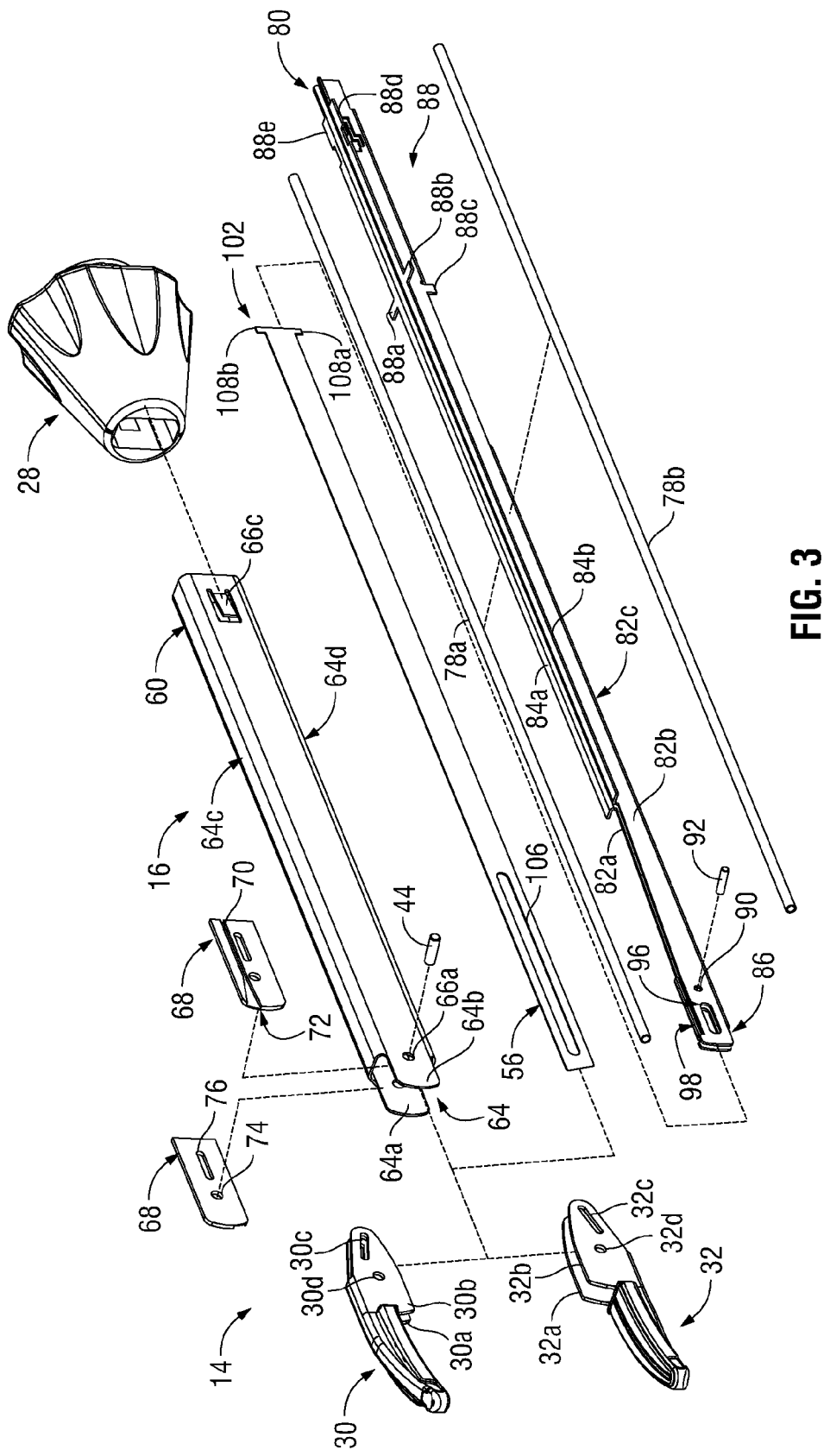
FIG. 3 is a perspective view of the end effector and elongated shaft of FIG. 1 with parts separated.

Referring now to FIG. 3, the elongated shaft 16 includes various longitudinal components that operatively couple the end effector 14 to the various actuators supported by the housing 12 (FIG. 1). An outer shaft member 60 defines an exterior surface of the elongated shaft 16 and supports movement of other components therethrough as described below. The outer shaft member 60 may be constructed from a flat stock piece of metal. In constructing the outer shaft member 60, a stamping, punching or similar metal-working process may be employed to initially generate a flat blank that includes an appropriate outer profile and any interior openings or features. Thereafter, the necessary folds, bends and curves, etc., may be formed by bending the flat blank with a press brake, or other suitable metal-working equipment. In some instances, folds, bends and curves may be formed in metal components simultaneously with the outer profile and interior openings, or with the same equipment employed for forming the outer profile and interior openings. Thus, a reference to a stamping process may be understood to include the formation of a flat profile, as well as imparting any curves, rolls or bends, etc., to the relevant component. The outer shaft member 60 may be formed by folding the flat blank into a generally rectangular profile such that two opposing longitudinal edges of the flat blank meet at a longitudinal seam 62 (see FIG. 4). The longitudinal seam 62 may be joined by laser welding (or other suitable processes) the two opposing longitudinal edges together to form a continuous rectangular profile. The seam 62 may be generally straight as depicted, or alternatively, a box joint, a dovetail joint or other interfaces known in the metal-working arts may be defined along the seam 62.

The outer shaft member 60 defines a clevis 64 at a distal end thereof for receiving the jaw members 30 and 32. Opposing vertical sidewalls 64a and 64b of the outer shaft member 60 extend distally of horizontal walls 64c and 64d and include respective bores 66a, 66b extending therethrough. The bores 66a, 66b frictionally support the pivot pin 44 and maintain an orientation of the pivot pin 44 with respect to the outer shaft member 60. Alternatively or additionally, the pivot pin 44 may be fastened to the outer shaft member 60 by laser or heat-based welding, adhesives, chemical bonding, or other suitable processes.

At a proximal end of the outer shaft member 60, a pair of tabs 66c (only one visible in FIG. 3) are provided to couple the outer shaft member 60 to the rotation knob 28. The connection established between the outer shaft member 60 and the rotation knob is described below with reference to FIGS. 5 and 6.

The pivot pin 44 extends through a proximal portion of each of the jaw members 30, 32 to pivotally support the jaw members 30, 32 at the distal end of the outer shaft member 60. As described in greater detail below with reference to FIG. 12, a proximal portion of each of the jaw members 30, 32 is configured as a "double flag" (alternately referred to as a "double flange"). The double flag configuration refers to the two laterally spaced parallel flanges or "flags" 30a, 30b and 32a, 32b respectively, extending proximally from a distal portion of the jaw members 30 and 32. A lateral cam slot 30c and a lateral pivot bore 30d extend through each of the flags 30a, 30b of the upper jaw member 30. Similarly, a lateral cam slot 32c and a lateral pivot bore 32d extend through each of the flags 32a, 32b of the lower jaw member 32. The pivot bores 30d, 32d receive the pivot pin 44 in a slip-fit relation that permits the jaw members 30, 32 to pivot about the pivot pin 44 to move the end effector 14 between the open and closed configurations (FIGS. 2A and 2B respectively).

A distal portion of each of the jaw members 30, 32 extends distally of the outer shaft member 60. The distal portion of each of the jaw members 30, 32 may be curved to facilitate manipulation of tissue and to provide better "line of sight" for accessing organs and large tissue structures. As depicted in FIG. 3, the jaw members 30, 32 curve to the left from the perspective of a user. As described in greater detail below with reference to FIG. 8, for example, the end effector 14 may be rotated about the longitudinal axis A-A such that the jaw members 30, 32 curve to the right. In some alternative embodiments, as described below with reference to FIG. 28, for example, and end effector 220 may be rotated to a stable orientation where jaw members 222, 224 curve in an upward direction.

A pair of wire guides 68 are provided to protect the wires 46a, 46b (FIG. 4) The wire guides 68 are positioned adjacent interior surfaces of the opposing vertical sidewalls 64a and 64b of the outer shaft member 60. Adhesives, screws or similar fastening mechanisms may be employed to affix the wire guides 68 such that position of the wire guides 68 may be maintained. In some alternative embodiments, as described below with reference to FIG. 23, wire guides 68 may be eliminated and structures may be incorporated into nearby components which may serve as wire guides.

The wire guides 68 are generally flat and may be constructed of metal, a lubricious plastic such as polytetrafluoroethylene (PTFE) or similar material. The wire guides 68 may thus provide a bearing surface for the exterior surfaces of flags 32a and 32b of the lower jaw member 32 as the jaw members 30, 32 pivot about the pivot pin 44. The wire guides 68 include a longitudinal passageway 70 through which a respective one of the wires 46a, 46b (FIG. 4) may extend to connect the sealing plates 48, 50 (FIG. 2A) to the electrosurgical generator 40 (FIG. 1). The passageways 70 maintain the wires against the sidewalls 64a, 64b of the clevis 64 to discourage entanglement of the wires due to motion of the various components within the elongated shaft 16. A distal flare 72 is provided in the passageways 70 to provide clearance for the wires to move with the jaw members 30, 32 as the jaw members 30, 32 pivot. Holes 74 are provided in the wire guides 68 to permit passage of the pivot pin 44 therethrough, and slots 76 are provided to guide motion of a cam pin 92 as described below with continued reference to FIG. 3. The slots 76 are optional and may be excluded from the wire guides 68 in some alternative embodiments where the cam pin 92 is sufficiently short. The holes 74 and the slots 76 are disposed on a central axis of the wire guides 68, and thus, two identical wire guides 68, oriented oppositely, may provide proper alignment with the holes 66a and 66b on outer shaft member 60.

A pair of wire conduits 78a and 78b may be provided to guide wires 46a and 46b (FIG. 4) proximally of the wire guides 68. The wire conduits 78a, 78b may be constructed of a plastic tube, and serve to protect the wires 46a, 46b from sharp edges that may form on surrounding components. The wire conduits 78a, 78b may also provides some rigidity to facilitate feeding the wires 46a, 46b into position during assembly.

A jaw drive rod 80 is received within the outer shaft member 60 and is configured for longitudinal motion with respect to the outer shaft member 60. The jaw drive rod 80 is constructed from a flat, metal stock piece, and may be formed by a stamping process similar to the formation of the outer shaft member 60 as described above. The jaw drive rod 80 generally exhibits a U-shaped profile including sidewalls 82a, 82b and a u-shaped connector portion 82c. Horizontal flanges 84a and 84b protrude laterally from the respective sidewalls 82b and 82a and laterally support the jaw drive rod within the outer shaft member 60. A distal portion 86 of the jaw drive rod 80 is configured for receipt within the outer shaft member 60 and includes features for operatively coupling the jaw drive rod 80 to the end effector 14. A proximal portion 88 of the jaw drive rod 80 is configured for receipt within the housing 12 (FIG. 1), and includes features for operatively coupling the jaw drive rod 80 to the actuators supported thereon, e.g. the movable handle 22.

The distal portion 86 of the jaw drive rod 80 includes a round hole 90 extending through the sidewalls 82a, 82b for receiving the cam pin 92. The cam pin 92 may be friction fit, welded or otherwise fastened within the hole 90 such that the cam pin 92 is fixedly coupled to the jaw drive rod 80 and protrudes laterally from each of the sidewalls 82a and 82b. Distally of the hole 90, a longitudinal slot 96 is defined through the sidewalls 82a, 82b. The longitudinal slot 96 provides clearance for the pivot pin 44, and thus, permits longitudinal reciprocation of the jaw drive rod 80 independent of the pivot pin 44.

An overfold 98 is defined in the vicinity of the hole 90 and the slot 96. A portion of the sidewall 82b is folded toward the opposing sidewall 82a such that a portion of the jaw drive rod 80 exhibits a generally closed profile in the vicinity of the overfold 98. As described in greater detail below with reference to FIG. 4, the overfold 98 permits the jaw drive rod 80 to serve as a knife guide to guide the motion of a knife 102.

The proximal portion 88 of the jaw drive rod 80 includes a set of laterally protruding collar stops 88a, 88b and 88c, and a pair of laterally protruding spring stops 88d, 88e. The collar stops 88a, 88b, 88c engage a drive collar 184, and the spring stops 88d, 88e engage a spring keeper 192, which, as described below with reference to FIG. 18, cooperate to operatively couple the jaw drive shaft 80 to the movable handle 22.

The knife 102 is a generally flat, metal component defining a profile that may be constructed by a stamping process as described above. The knife 102 supports the sharpened knife blade 56 at a distal-most end thereof. The sharp edge of the knife blade 56 may be applied to the distal end of the knife 102 subsequent to the stamping process that forms the profile. For example, various manufacturing techniques may be employed such as grinding, coining, electrochemical etching or other suitable manufacturing processes for forming sharpened edges. A longitudinal slot 106 is defined with the knife 102 to provide clearance for the pivot pin 44 and the cam pin 92. Proximal tabs 108a, 108b protrude from the knife 102 and provide a mechanism for operatively coupling the knife 102 to the trigger 26. The connection between the knife 102 and the trigger 26 is described in detail below with reference to FIGS. 19 and 20.

Figure 4:
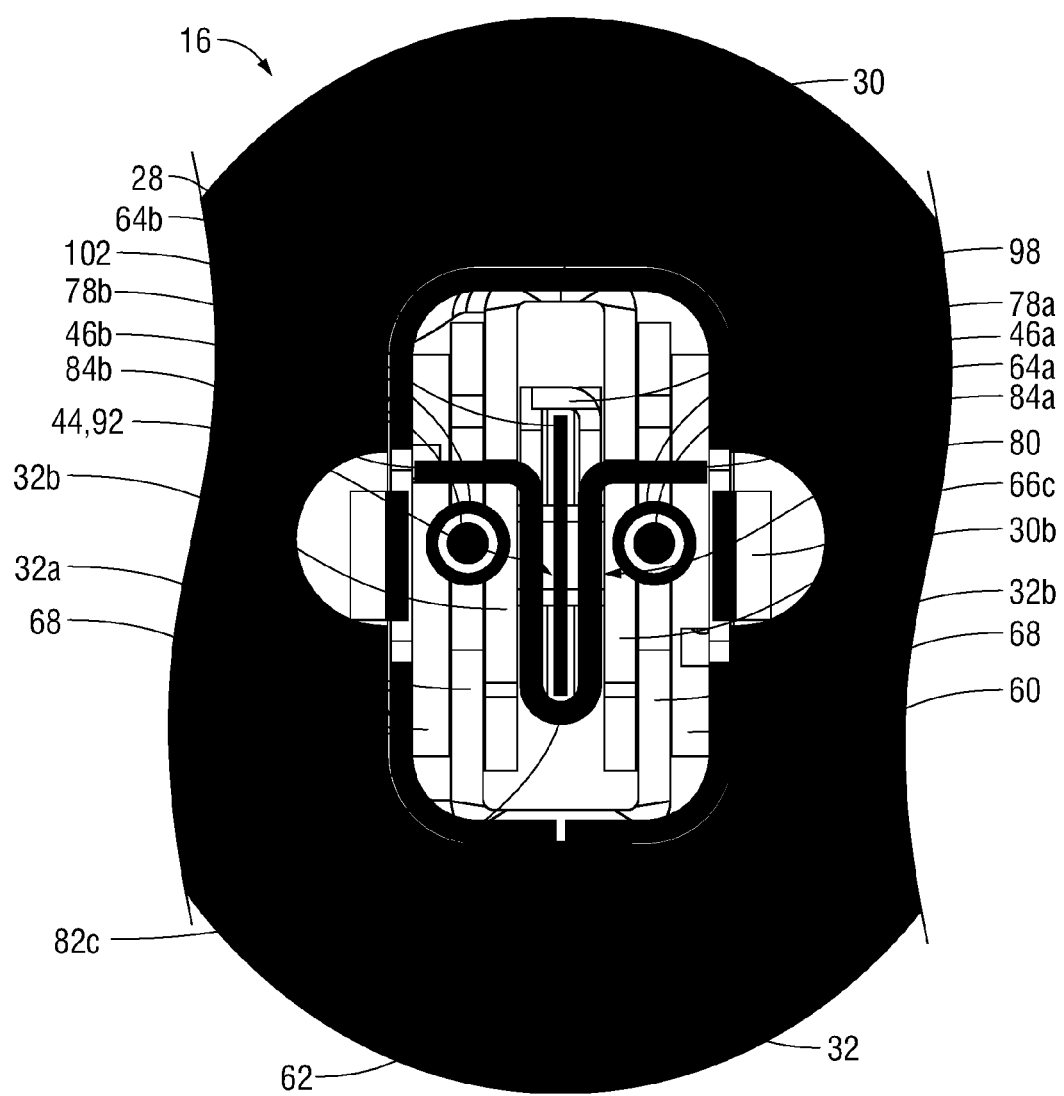
FIG. 4 is cross-sectional view of the elongated shaft if FIG. 1 taken through a plane that extends through an interface between the elongated shaft and a rotation knob, facing a proximal end of the jaw members.

Referring now to FIG. 4, the various components of the elongated shaft 16 are depicted assembled to one another and to the upper and lower jaw members 30, 32. The outer shaft member 60 is secured to the rotation knob 28 by the engagement of the tabs 66c on the outer shaft member 60 with the rotation knob 28 (see also, FIG. 6). The jaw drive rod 80 is positioned within the outer shaft member 60 such that the horizontal flanges 84a and 84b of the jaw drive rod 80 abut the sidewalls 64a and 64b of the outer shaft member 60. The wire guides 68 are positioned between the sidewalls 64a and 64b of the outer shaft member 60 and the flags 32a, 32b of the lower jaw member 32, thus, providing lateral support to the lower jaw member 32. The flags 30a, 30b of the upper jaw member 30 are disposed laterally within the flags 32a, 32b of the of the lower jaw member 32. This arrangement of flags 30a, 30b laterally within the flags 32a, 32b may be described as a "nestled" arrangement. Other arrangements are contemplated such as the "offset" arrangement described below with reference to FIG. 15.

The knife 102 is centrally disposed within the jaw drive shaft 80. The sidewalls 82a, 82b of the jaw drive shaft 80 provide lateral support to the knife 102, and vertical support is provided by the u-shaped connector portion 82c and the over-fold 98. The knife 102 is substantially surrounded at its distal end by the jaw drive shaft 80 on four lateral sides, and by substantially surrounding the knife 102 at its distal end, the jaw drive shaft 80 constrains the motion of the knife 102 in the four lateral directions. Free motion of the knife 102 is permitted only in a longitudinal direction. Thus, the jaw drive shaft 80 serves as a knife guide by urging the knife 102 into a central position within the elongated shaft 16, and thus ensuring proper alignment of the knife 102 as the knife 102 reciprocates within knife channel 58 (FIG. 2A). By substantially surrounding the knife 102 at its distal end, the jaw drive rod 80 restricts movement of the knife 102 in two orthogonal lateral planes, e.g. a vertical and a horizontal plane. The jaw drive rod 80 may also serve to protect the knife 102 and other components from damage throughout the assembly of the elongated shaft 16 and jaw members 30, 32.

Figure 5:
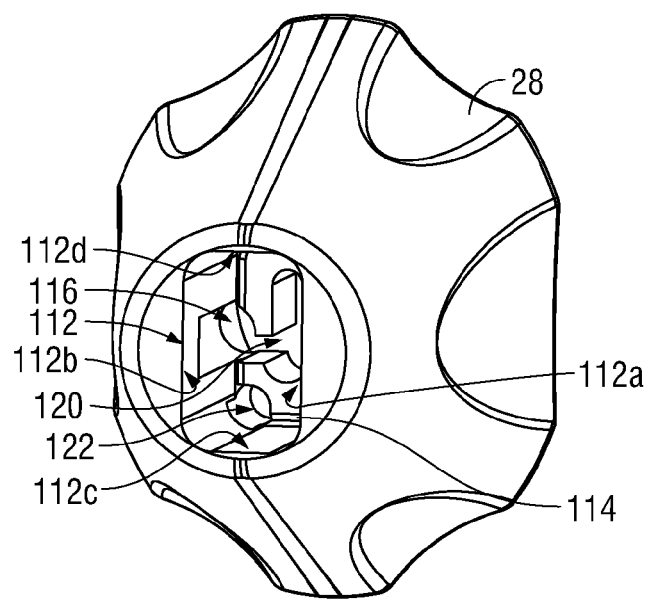
FIG. 5 is a proximally-facing perspective view of a rotation knob depicting a cavity for receiving an the elongated shaft of FIG. 1.
Figure 6:
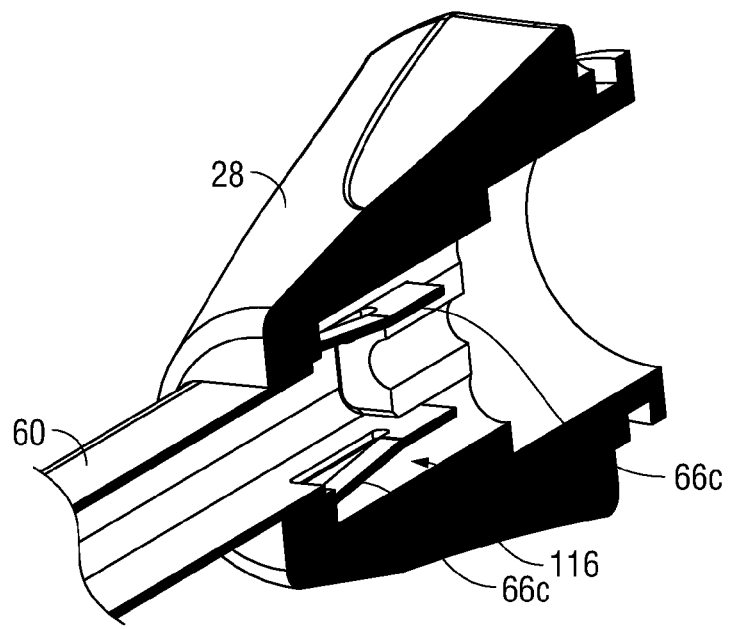
FIG. 6 is a cross-sectional, perspective view of the rotation knob of FIG. 5 assembled to an outer shaft member of the elongated shaft of FIG. 1.

Referring now to FIGS. 5 and 6, the rotation knob 28 is configured as a single component. In some alternative embodiments, as described below with reference to FIG. 25, for example, a rotation knob 260 may be provided that is constructed of multiple components affixed to one another. The rotation knob 28 includes a distal opening 112 defined therein for receiving the outer shaft member 60. The distal opening 112 is bounded by lateral walls 112a, 112b, 112c and 112d, which define a generally rectangular profile corresponding to the rectangular profile of the outer shaft member 60. The distal opening 112 includes an interior landing 114 for seating a proximal-most surface of the outer shaft member 60 and two lateral latch pockets 116 for receiving the tabs 66c of the outer shaft member 60. The tabs 66c are flexible and project laterally outward in a distal direction such that the insertion of the proximal end of the outer shaft member 60 onto the distal opening 112 of the rotation knob 28 induces the tabs to flex inwardly momentarily as the tabs 66c engage lateral walls 112a, 112b, and then return to the outwardly projecting orientation inside the latch pockets 116. The tabs 66c thus lock the outer shaft member 60 to the rotation knob 28. Due to the rectangular profile of the outer shaft member 60 and the opening 112, rotational motion imparted to the rotation knob 28 about the longitudinal axis A-A (FIG. 1) is transferred to the outer shaft member 60.

A passageway 120 is defined through the rotation knob 28 to permit longitudinal motion of the jaw drive shaft 80 (FIG. 3) therethrough. The passageway 120 is shaped such that rotational motion imparted to the rotation knob 28 is transferred to the jaw drive shaft 80. In one embodiment, a cable clearance passageway 122 is also defined through rotation knob 28 to permit passage of electrical cables (e.g., 46a, 46b, FIG. 4) that electrically couple the sealing plates 48, 50 (FIG. 2A) to the electrosurgical generator 40 (FIG. 1). Rotational motion imparted to the rotation knob 28 may thus impart rotational motion to each of the components of the elongated shaft 16, and to the end effector 14, which is coupled thereto.

Figure 7:
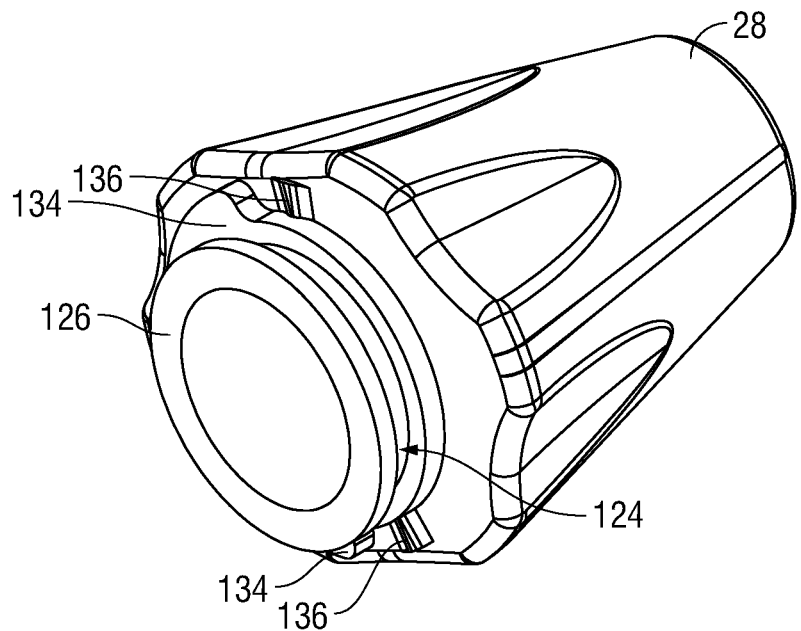
FIG. 7 is a distally-facing perspective view of the rotation knob of FIG. 5 depicting a groove for receiving a portion of the housing of FIG. 1.
Figure 8:
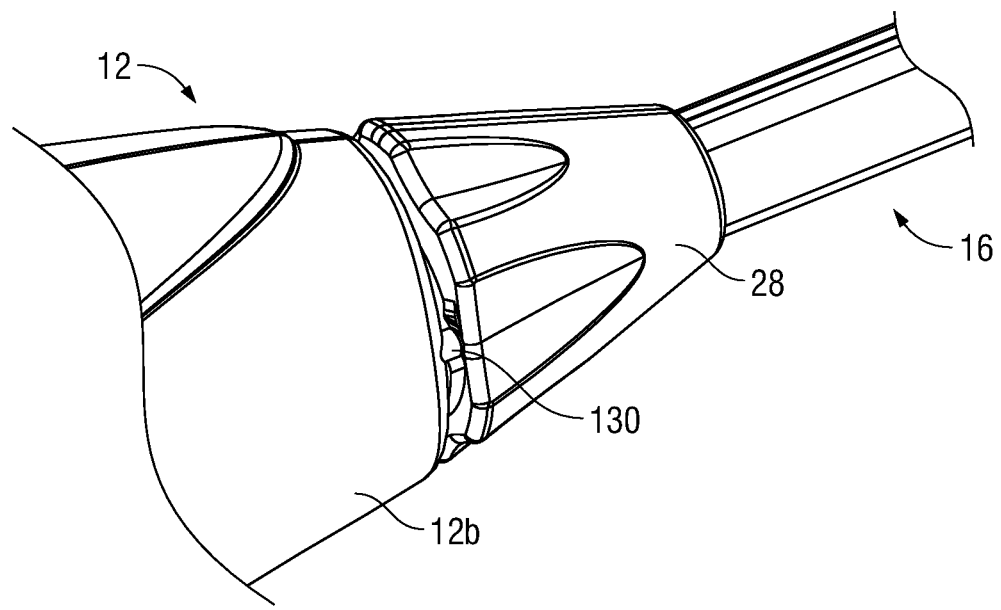
FIG. 8 is a perspective view of the rotation knob of FIG. 5 assembled to the housing of FIG. 1.

Referring now to FIGS. 7 and 8, a proximal end of the rotation knob 28 is configured to engage the housing 12. A circular groove 124 is defined around a circular boss 126 projecting proximally from the rotation knob 28. The circular groove 124 receives an inwardly projecting wall (not visible) of the housing 12 to maintain the rotation knob 28 against the distal end of the housing 12. The circular groove 124 guides the rotational motion of the rotation knob 28 about the longitudinal axis A-A (FIG. 1).

The rotational motion of the rotation knob 28 may be limited by a stop boss 130 projecting distally from the housing 12. The stop boss 130 is positioned to engage rotation stops 134 on the rotation knob 28 to prevent rotational motion of the rotation knob further than, for example, 180 degrees in either direction. Detents 136 project proximally from the rotation knob 28 to engage a distal surface of the stop boss 130 prior to the stop boss 130 engaging the rotation stops. When the rotation knob 28 is rotated to a position wherein the stop boss 130 is positioned between a rotation stop 134 and a detent 136, the rotational position of the rotation knob 28 is relatively stable, and may be releasably maintained until a sufficient force is supplied to move the detents 136 over the stop boss 130. Two radially opposite positions are defined wherein the rotational position of the rotation knob 28 is relatively stable. These two radially opposite positions correspond with two orientations of the end effector 14 (FIG. 1) in which the jaw members 30, 32 curve to the right and to the left from the perspective of a user.

Figure 9:
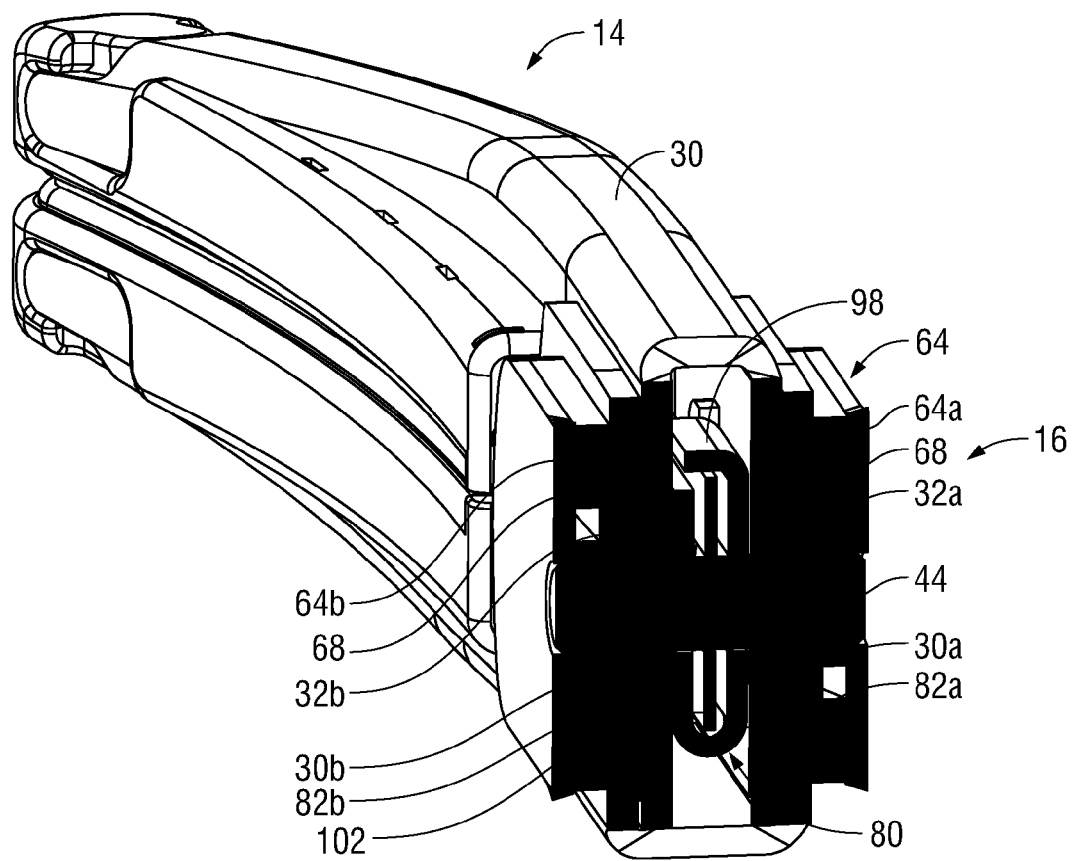
FIG. 9 is a cross-sectional, perspective view of the end effector assembled with the elongated shaft of FIG. 1.

Referring now to FIG. 9, the end effector 14 is coupled to the distal end of the elongated shaft 16 by the pivot pin 44. The pivot pin 44 is coupled to the sidewalls 64a and 64b of the clevis 64 defined at the distal end of the outer shaft member 60. Thus, the pivot pin 44 represents a longitudinally stationary reference for the longitudinal movements of jaw drive rod 80 and the knife 102. Laterally inward of the sidewalls 64a, 64b, the pivot pin 44 extends through the wire guides 68, the flags 32a, 32b of the lower jaw member 32, the flags 30a and 30b of the upper jaw member 30, the sidewalls 82a, 82b of the jaw drive shaft 80, and the knife 102. The jaw members 30, 32 are free to pivot about the pivot pin 44, and the jaw actuation shaft 80 and the knife 102 are free to translate longitudinally around the pivot pin 44.

Figure 10:
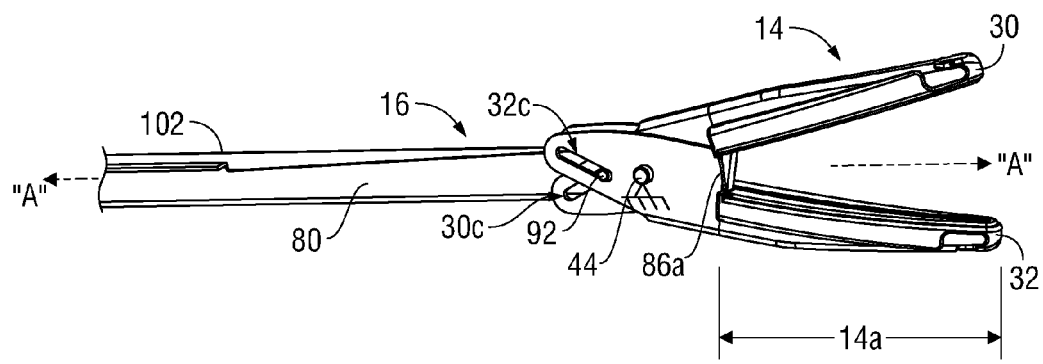
FIG. 10 is a partial, perspective view of a distal portion of a jaw actuation mechanism of the end effector of FIG. 1.

Referring now to FIG. 10, the jaw drive rod is 80 is disposed in a distal position maintaining the end effector 14 in the open configuration. Since the jaw drive rod 80 is coupled to the cam pin 92, when the jaw drive rod 80 is in the distal position, the cam pin 92 is located in a distal position in cam slots 30c and 32c defined through the flags 30a, 30b, 23a, 32b of the jaw members 30, 32. Also, when the jaw drive rod 80 is in the distal position, a distal-most face 86a of the jaw drive rod 80 extends to a tissue receiving region 14a of the end effector 14. Thus, the jaw drive rod 80 provides a stop to prevent the entry of tissue into the elongated shaft 16.

The jaw drive rod 80 may be drawn proximally relative to the pivot pin 44 (the stationary longitudinal reference) to move the end effector 14 to the closed configuration (see FIG. 2B). Since the longitudinal position of the pivot pin 44 is fixed (by the outer shaft member 60, which is removed from view in FIG. 10 for clarity), and since the cam slots 30c, 32c are obliquely arranged with respect to the longitudinal axis A-A, proximal retraction of the cam pin 92 through the cam slots 30c, 32c induces the jaw members 30, 32 to pivot toward one another about the pivot pin 44. Conversely, when the end effector 14 is in the closed configuration, longitudinal translation of the jaw drive rod 80 in a distal direction induces the jaw members 30, 32 to pivot away from one another toward the open configuration.

Figure 11:
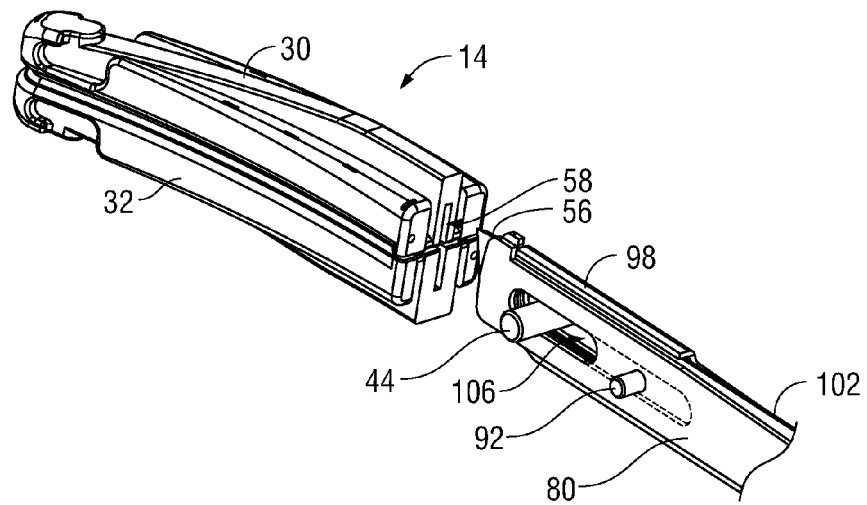
FIG. 11 is a partial, perspective view of distal portion of a knife actuation mechanism of the end effector of FIG. 1.

Referring now to FIG. 11, when the end effector 14 is in the closed configuration, the knife 102 is freely movable in a longitudinal direction within the jaw drive shaft 80. The slot 106 in the knife 102 extends around the both the pivot pin 44 and the cam pin 92, and thus the pins 44, 92 do not interfere with the reciprocal motion of the knife 102. The blade 56 at the distal-most end of the knife 102 is centrally aligned by the distal-most end of the jaw drive rod 80 that includes the fold-over 98. Properly aligned, the blade 104 readily enters the knife channel 58 defined in the jaw members 30, 32. The portion of the knife 102 extending distally from the jaw drive rod 80 is free to bend and, thus, the blade 104 follows the curvature of the knife channel 58 through the jaw members 30, 32 as the knife 102 reciprocates longitudinally.

Referring now to FIGS. 12 and 13, the lower jaw member 32 is constructed of three major components. These components include a double-flag jaw insert 140, an insulator 142 and the sealing plate 48. In some alternative embodiments, as described below with reference to FIG. 22, for example, a jaw member 224 may be provided that is constructed of major components arranged to provide unique advantages.

The flags 32a, 32b of the jaw member 32 define a proximal portion of the double-flag jaw insert 140, and a generally u-shaped channel 144 extends distally to support the tissue engaging portion of the jaw member 32. The double-flag jaw insert 140 includes various planar surfaces, and may be constructed as a sheet metal component formed by a stamping process as described above. In such a stamping process, the cam slots 32c and pivot holes 32d may be punched into a flat blank, and subsequently the blank may be bent to form the flags 32a, 32b and the u-shaped channel 144. A lateral bend may also be applied to the jaw insert 140 to accommodate the curvature of the jaw member 32.

The insulator 142 may be constructed of an electrically isolative plastic such as a polycarbonate (PC), acrylonitrile butadiene styrene (ABS), or a blend (PC/ABS) thereof. The electrically isolative plastic may be overmolded onto the jaw insert 140 in a single-shot injection molding process. Various features may be molded into the insulator 142 that facilitate the attachment of the sealing plate 48 to the insert 140. For example, tabs may be provided that permit a snap-fit attachment of the sealing plate 48, or ridges may formed that permit ultrasonic welding of the sealing plate onto the insulator 142. The sealing plate 50 may be constructed of an electrically conductive metal, and may be stamped from a flat sheet stock.

Referring now to FIG. 14, the flags 30a, 30b of the upper jaw member 30 are depicted schematically in a nestled configuration with respect to the flags 32a, 32b of the lower jaw member 32. A. The proximal portion of the upper jaw member 30 is narrower than the proximal portion of the lower jaw member 32, and thus, a lateral spacing "S" between the flags 32a, 32b is sufficient to permit the flags 30a and 30b to be positioned therebetween. A pivot axis "P0" extends through an overlapping portion of the flags 30a, 32a, and 30b, 32a such that the upper and lower jaw members 30, 32 may pivot about the common axis "P0." In the nestled configuration, the proximal portions of the upper and lower jaw members 30, 32 also share a common centerline "CL-1" that is transverse with respect to the pivot axis "P0."

An alternative to the nestled configuration illustrated in FIG. 14 is the offset configuration illustrated schematically in FIG. 15. A proximal portion of double-flag upper jaw member 150 includes flags 150a and 150b. A proximal portion of a double-flag lower jaw member 152 includes flags 152a and 152b and exhibits a width that is identical to a width of the proximal portion of the upper jaw member 150. To provide an overlapping portion of the flags 150a, 152a and 150b, 152b such that the jaw members 150, 152 may pivot about the common axis "P0," one flag 150a of the upper jaw member 150 is positioned on a laterally exterior side of the corresponding flag 152a of the lower jaw member 152, and the other flag 150b of the upper jaw member 150 is positioned on a laterally interior side of the corresponding flag 152b of the lower jaw member 152. In the offset configuration, a centerline "CL-2" of the proximal portion of the upper jaw member 150 is laterally offset with respect to a centerline "CL-3" of the lower jaw member 152.

In embodiments where a distal, tissue engaging portion (depicted in phantom) of the jaw members 150, 152 is generally straight, e.g., without the lateral curve of jaw members 30, 32 (see, e.g., FIG. 2B), the offset configuration permits the jaws 150 and 152 to be constructed as substantially identical components. The straight distal portions of the jaw members 150, 152 may be aligned along a common centerline "CL-4" although proximal portions of the jaw members 150, 152 are aligned along their respective centerlines "CL-2" and "CL-3." Generally, a forceps with identically configured jaw members 150, 152 may be relatively economical to produce.

Figure 16:
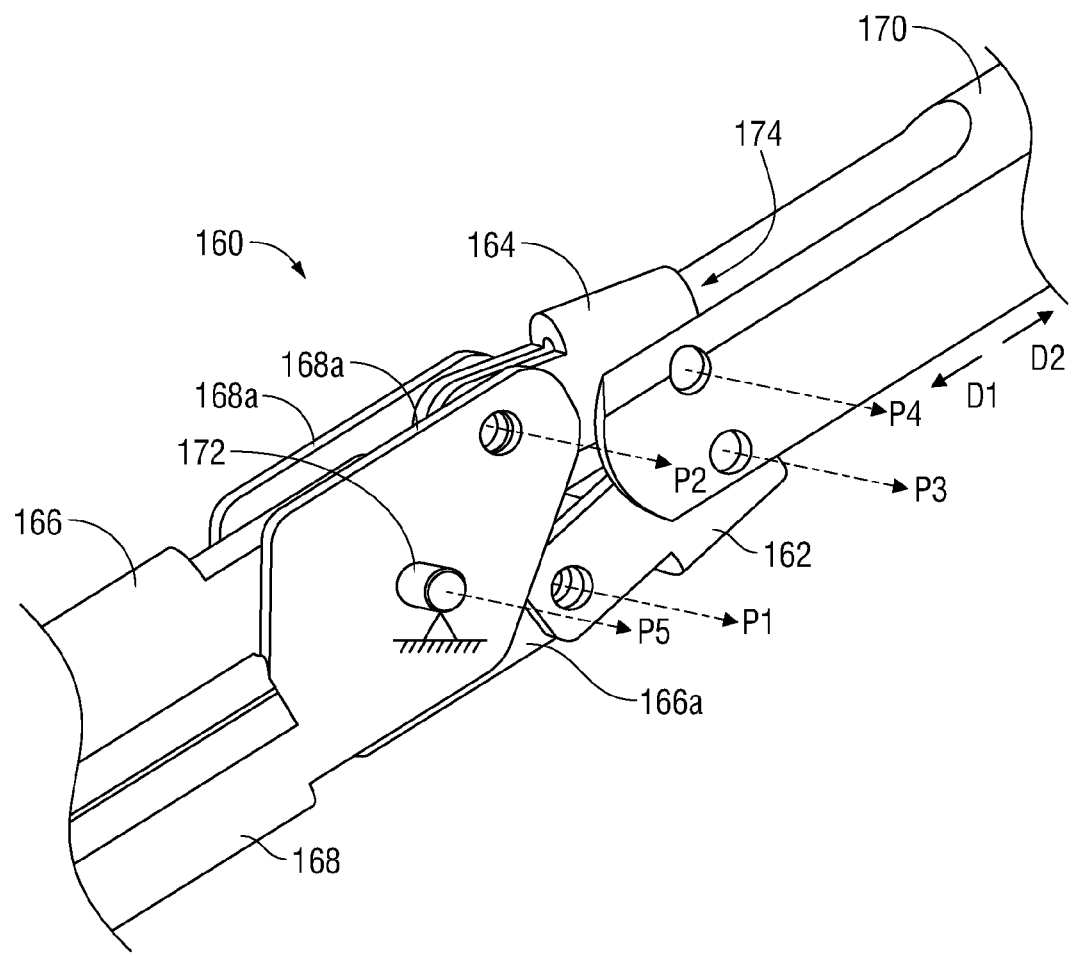
FIG. 16 is a partial, perspective view of an alternate embodiment of a jaw actuation mechanism depicting an alternate pair of jaw members with a nestled arrangement of double flanges coupled to an reciprocating actuation rod by stamped links.

Referring now to FIG. 16, an alternate embodiment of an actuation mechanism 160 is depicted. The actuation mechanism 160 employs a pair of stamped lever links 162, 164 for opening and closing a pair of jaw members 166, 168. An upper jaw member 166 includes a proximal flange 166a pivotally coupled to a lower lever link 162 about pivot axis "P1." A lower jaw member 168 includes proximal flanges 168a pivotally coupled to an upper lever link 164 about pivot axis "P2." Each of the proximal flanges 166a and 168a may also be constructed as stamped metal components as described above. The lever links 162, 164 are pivotally coupled to a reciprocating drive rod 170 about respective pivot axes "P3" and "P4" and each of the proximal flanges 166a, 168a is pivotally coupled about a pivot pin 172, which is arranged about a pivot axis "P5." The pivot pin 172 is coupled to an outer shaft member (not shown), and thus represents a fixed reference for the motion of the motion of the actuation mechanism 160.

The reciprocating drive rod 170 is movable in a distal longitudinal direction as indicated by arrow "D1" and a proximal longitudinal direction, as indicated by arrow "D2." Since the longitudinal position of the pivot pin 172 is fixed, longitudinal movement of the reciprocating drive rod 170 induces the link 162 to pivot simultaneously about axes "P1" and "P3," and induces link 164 to pivot simultaneously about axes "P2" and "P4." This simultaneous pivoting of the links 162, 164 induces the jaw members 166, 168 to pivot about the axis "P5" between the closed configuration depicted and an open configuration (not shown).

The double flag jaw members 166, 168 include proximal flanges 166a, 168a arranged in a nestled configuration (see FIG. 14). The upper link 164 may also be characterized as "nestled," or disposed laterally between, the flags of proximal flange 168a of the lower jaw member 168. The proximal flange 166a of the upper jaw member 166 is "nestled" within the lower lever link 162. Each of the pivot links 162, 164 and the proximal flanges 166a, 168a include a generally u-shaped cross section to permit the pivot links 162, 164 to interleave with the proximal flanges 166a, 168a in this manner. This configuration provides a central channel 174 through which a knife or other centrally disposed drive component (not shown) may extend.

The actuation mechanism 160 allows the jaw members 166, 168 to open or separate from one another to a greater degree than an actuation mechanism for opening similarly sized jaw members employing a simple cam slot (see, e.g., FIG. 10). The actuation mechanism 160 also provides a tactile feel that some operators may prefer. The stamped lever links 162, 164 and proximal flanges 166a, 168a provide a relatively strong actuation mechanism 160, which permits the jaw members 166, 168 to apply a relatively large force to tissue captured therebetween.

Figure 17:
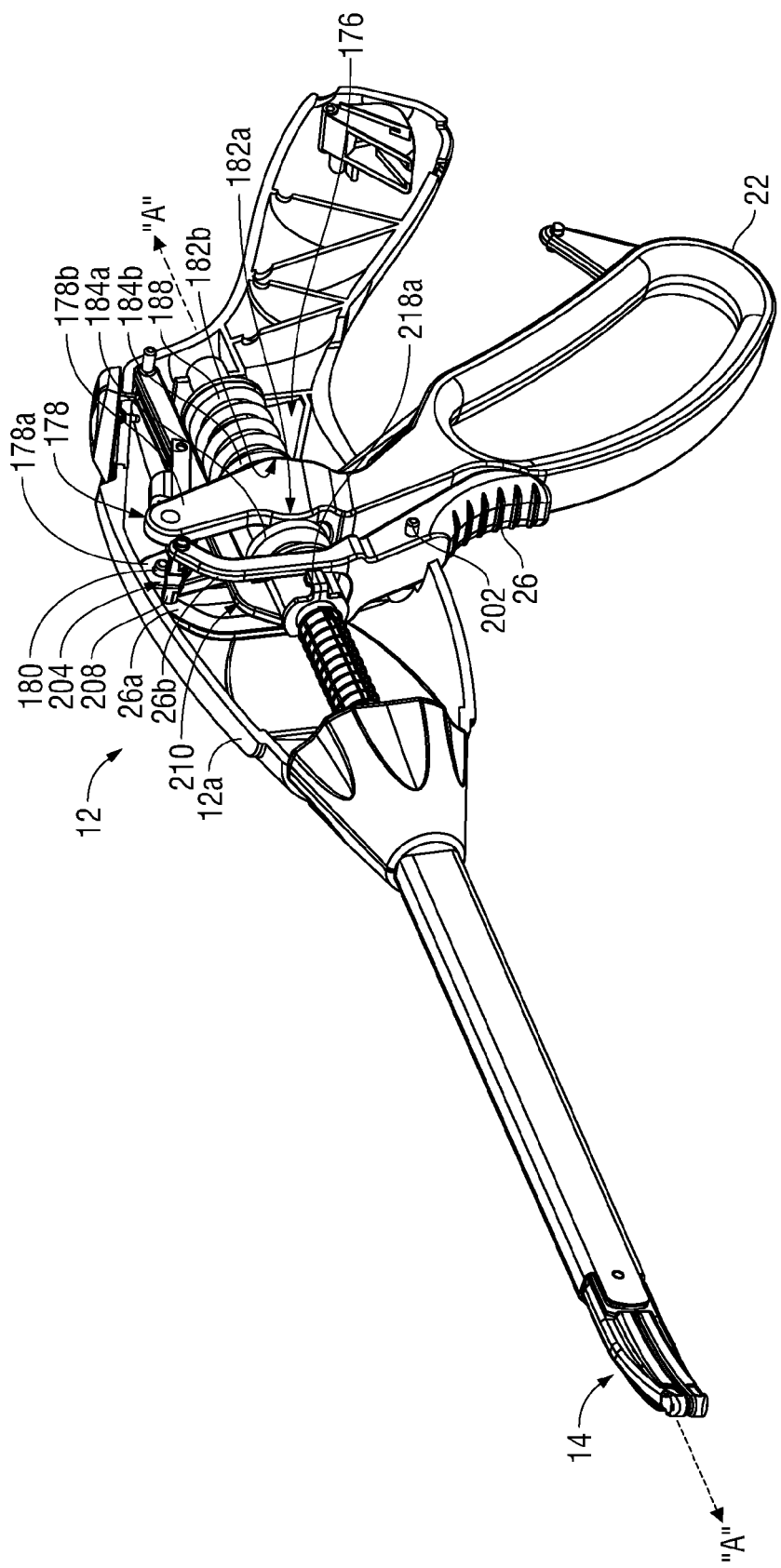
FIG. 17 is a perspective view of a proximal portion of the instrument of FIG. 1 with a portion of the housing removed revealing internal components.

Referring now to FIG. 17, the connection of the movable handle 22 and the knife trigger 26 to the longitudinally movable components of the elongated shaft 16 is described. The movable handle 22 may be manipulated to impart longitudinal motion to the jaw drive rod 80 (FIG. 10), and knife trigger 26 may be manipulated to impart longitudinal motion to the knife 102 (FIG. 11). As discussed above, longitudinal motion of the jaw drive rod 80 serves to move the end effector 14 between the open configuration of FIG. 2A and the closed configuration of FIG. 2B, and longitudinal motion of the knife 102 serves to move knife blade 56 through knife channel 58 (FIG. 2A).

Figure 18:
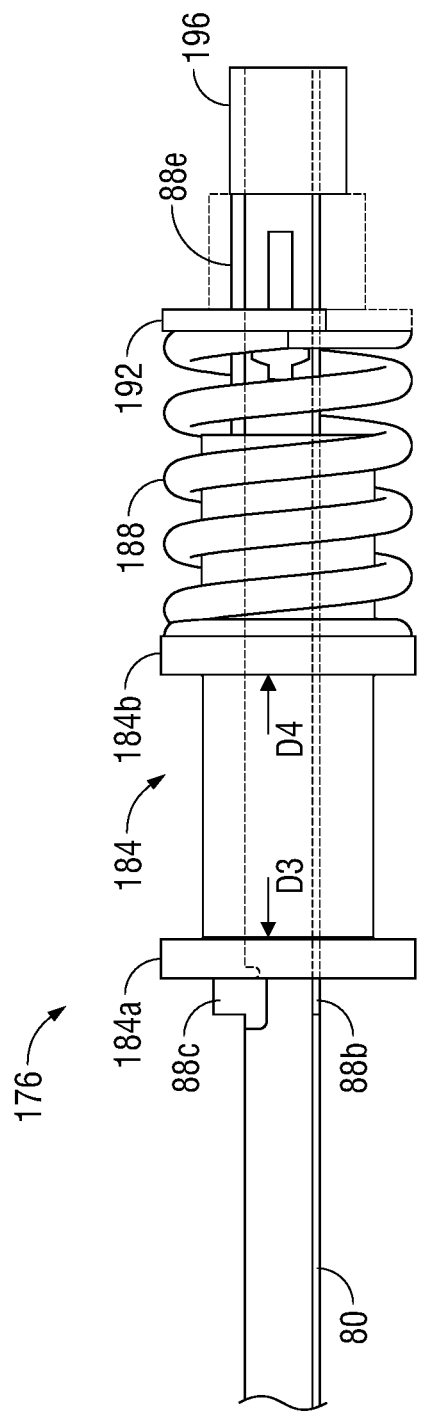
FIG. 18 is a partial, side view of a proximal portion of the jaw actuation mechanism of FIG. 10 depicting a connection between the handle and the jaw drive rod mechanism for imparting longitudinal movement to the jaw drive rod.

The movable handle 22 is operatively coupled to the jaw drive rod 80 by a connection mechanism 176. The connection mechanism 176 includes a clevis 178 defined at an upper end of the movable handle 22. The clevis 178 is pivotally supported on the right housing half 12a by a pivot boss 180. A second complementary pivot boss 180 (not shown) is provided on the left housing half 12b (FIG. 1) to support the clevis 178. Each of two upper flanges 178a and 178b of the clevis 178 include rounded drive surfaces 182a and 182b thereon for engaging respective rims 184a and 184b of a drive collar 184 (FIG. 18). The drive surfaces 182a, 182b are arranged along the longitudinal axis A-A such that pivotal motions of the movable handle 22 about the pivot bosses 180 induce corresponding longitudinal motions of the drive collar 184 along the longitudinal axis A-A.

Referring now to FIG. 18, a distal longitudinal motion may be imparted to the connection mechanism 176 by pushing the distal rim 184a of the drive collar 184 with the movable handle 22 (FIG. 17) as indicated by arrow D3. The distal rim 184a engages the collar stops 88a (FIG. 3), 88b and 88c. Thus, the distal longitudinal motion of the drive collar 184 will be transmitted directly to the jaw drive rod 80 to induce a corresponding distal motion of the jaw drive rod 80. A proximal longitudinal motion may be imparted to the connection mechanism 176 by pushing the proximal rim 184b of the drive collar 184 with the movable handle 22 (FIG. 17) as indicated by arrow D4. The proximal rim 184b engages a compression spring 188, which is constrained between the proximal rim 184b and a spring keeper 192. The spring keeper 192 engages the spring stops 88d (FIG. 3) and 88e of the jaw drive rod 80. Thus, the proximal motion of the drive collar 184 is transmitted to the jaw drive rod 80 through the compression spring 188 and the spring keeper 192.

Proximal movement of the jaw drive rod 80 draws the cam pin 92 proximally to pivot the jaw members 30, 32 toward one another to move the end effector 14 to the closed configuration as described above with reference to FIG. 10. Once the jaw members 30 and 32 are closed, the jaw drive rod 80 essentially bottoms out (i.e., further proximal movement of the jaw drive rod 80 is prohibited since the jaw members 30, 32 contact one another). Further proximal movement of the movable handle 22 (FIG. 17), however, will continue to move the drive collar 184 proximally. This continued proximal movement of the drive collar 184 compresses the spring 188. When compressed, the spring 188 imparts additional force to the jaw drive rod 80, which results in additional closure force applied to tissue captured between the jaw members 30, 32 (see FIG. 2B). The spring 188 also serves to bias the jaw members 30, 32 and the movable handle 22 to the open configuration.

A rotation spacer 196 is supported at the proximal end of the jaw drive rod 80. The rotation spacer 196 includes an interior passageway (not shown) that receives the irregular cross-section of the jaw drive rod 80. An outer surface of the rotation spacer 196 is generally cylindrical, and thus, the rotation spacer 196 may support the proximal end of the jaw drive rod 80 within the housing 12 (see FIG. 17) through rotation of the elongated shaft 80 about the longitudinal axis A-A, e.g., rotation induced by rotation of the rotation knob 28 (FIG. 17). In some embodiments, e.g., where longitudinal translation between the rotation spacer 196 and spring keeper 192 is not required, the rotation spacer 196 and the spring keeper 192 may be constructed as a single component as depicted in phantom. The single component spring keeper 192 and rotation spacer 196 may be coupled to the jaw drive shaft 80 by a dowel pin (not shown).

Referring again to FIG. 17, the trigger 26 is pivotally supported in the housing 12 about a pivot boss 202 protruding from the trigger 26. The trigger 26 is operatively coupled to the knife 102 (FIG. 11) by a knife connection mechanism 204 such that pivotal motion of the trigger 26 induces longitudinal motion of the knife 102. The knife connection mechanism 204 includes upper flanges 26a, 26b of the trigger 26, a link 208, and a knife carriage 210. The link 208 is pivotally coupled to the flanges 26a, 26b and the knife carriage 210 such that pivotal motion of the trigger 26 induces longitudinal motion of the knife carriage 210.

Referring now to FIG. 19, the knife carriage 210 is longitudinally movable over the jaw drive rod 80 independently of the motion of the jaw drive rod 80. Thus, the jaw drive rod 80 may be regarded as a stationary reference for the movement of the knife carriage 210. The knife carriage 210 includes a sleeve 212, a knife arm 216, and a cap 218.

The knife arm 216 includes a pivot boss 216a, about which the link 208 (see FIG. 21C) is coupled to knife arm 216. As described below with reference to FIG. 21C, the link 208 imparts longitudinal movement to the knife carriage 210 in a distal direction of arrow A9. Guide arms 216b protrude laterally from the proximal end of the knife arm 216, and engage a respective guide slot 12c (shown schematically in FIG. 19 and visible in FIG. 21C) defined in the housing 12 to guide the longitudinal motion of the knife carriage 210.

The sleeve 212 is coupled to the knife arm 216, and thus, the sleeve 212 translates along with the knife bar 216. The sleeve 212 includes indentations or catches 212a defined therein, which receive snap-in arms 218a of the cap 218. The cap 218 may thus be assembled to the sleeve 212 such that cap 218 and the sleeve 212 translate together. Thus, the entire knife carriage 210, i.e., the knife bar 216, the sleeve 212 and the cap 218, may all be induced to translate together along the jaw drive rod 80 in the direction of arrow A9. The knife carriage 210 abuts a spring 219, which is compressed against the rotation knob 28 (shown schematically in FIG. 19) when the knife carriage 210 translates in the direction of arrow A9. The spring 219 biases the knife carriage 210 in a proximal direction to a proximal position along the jaw drive rod 80.

Referring now to FIG. 20, the knife 102 is coupled to the knife carriage 210 such that the longitudinal motion of the knife carriage 210 is transmitted to the knife 102. The proximal tabs 108a, 108b protruding from the knife 102 are captured between the sleeve 212 and the cap 218, and thus the knife 102 will translate with the knife carriage 210 in both the proximal and distal directions. The proximal tabs 108a, 108b are free to rotate about the longitudinal axis A-A within the sleeve 212, and thus, the knife 102 may rotate along with the jaw drive rod 80 within the knife carriage 210 when the rotation knob 28 is rotated as described above.

Figure 21A:
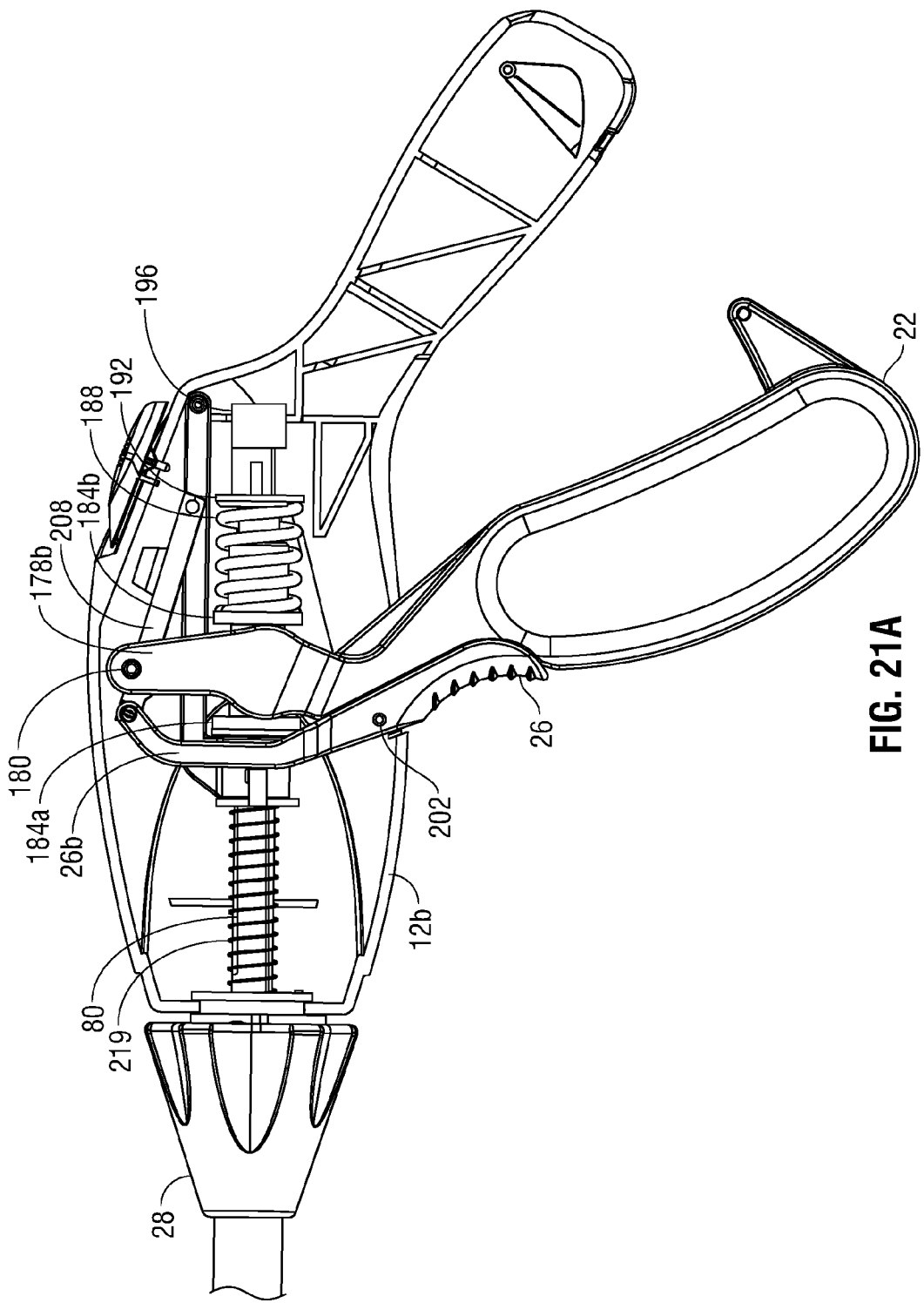
FIG. 21A is a side view of the proximal portion of the instrument of FIG. 17 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members.

Referring now to FIGS. 21A, 21B, 21C and 21D, a sequence of motions may be initiated by moving the movable handle 22 to induce motion in the jaw drive mechanism in order to close the jaws 30, 32, and by moving the trigger 26 to induce motion in the knife actuation mechanism in order to translate the bade 56 through the jaws 30, 32. Initially, both the moveable handle 22 and the knife trigger 26 are in a distal or un-actuated position as depicted in FIG. 21A. This arrangement of the moveable handle 22 and trigger 26 sustains the end effector 14 in the open configuration (FIG. 2A) wherein the jaw members 30, 32 are substantially spaced from one another, and the knife blade 56 is in a retracted or proximal position with respect to the jaw members 30, 32. The initial distal position of the trigger 22 is actively maintained by the influence of the spring 219 on the knife actuation mechanism. The distal position of the moveable handle 22, however, is only passively maintained, e.g., by internal friction within the jaw actuation mechanism. When both the moveable handle 22 and the knife trigger 26 are in the distal, un-actuated position, pivotal motion of the knife trigger 26 in a proximal direction, i.e., toward the stationary handle 20, is prohibited by interference between the trigger 26 and moveable handle 22. This interference prohibits advancement of the knife blade through the jaw members 30, 32 when the end effector 14 is in the open configuration.

The movable handle 22 may be moved from the distal position of FIG. 21A to the intermediate position depicted in 21B to move the jaw members 30, 32 to the closed configuration (FIG. 2B). As the movable handle 22 pivots about the pivot boss 180 in the direction of arrow M1, the drive surface 182b engages the proximal rim 184b of the drive collar 184. The drive collar 184, the spring 188 and the spring keeper 192 are all driven proximally against the spring stops 88d and 88e of the jaw drive rod 80, and thus, the jaw drive rod 80 is driven proximally in the direction of arrow M2. As discussed above with reference to FIG. 10, proximal movement of the jaw drive rod 80 serves to draw the cam pin 92 proximally though the cam slots 30c, 32c of the jaw members 30, 32 and thus pivot the jaw members 30, 32 toward one another. As the jaw members 30, 32 engage one another and no further pivotal movement of the jaw members 30, 32 may be achieved, the jaw actuation mechanism "bottoms out" and further proximal movement of the cam pin 92 and the jaw drive rod 80 is prohibited.

Figure 21B:
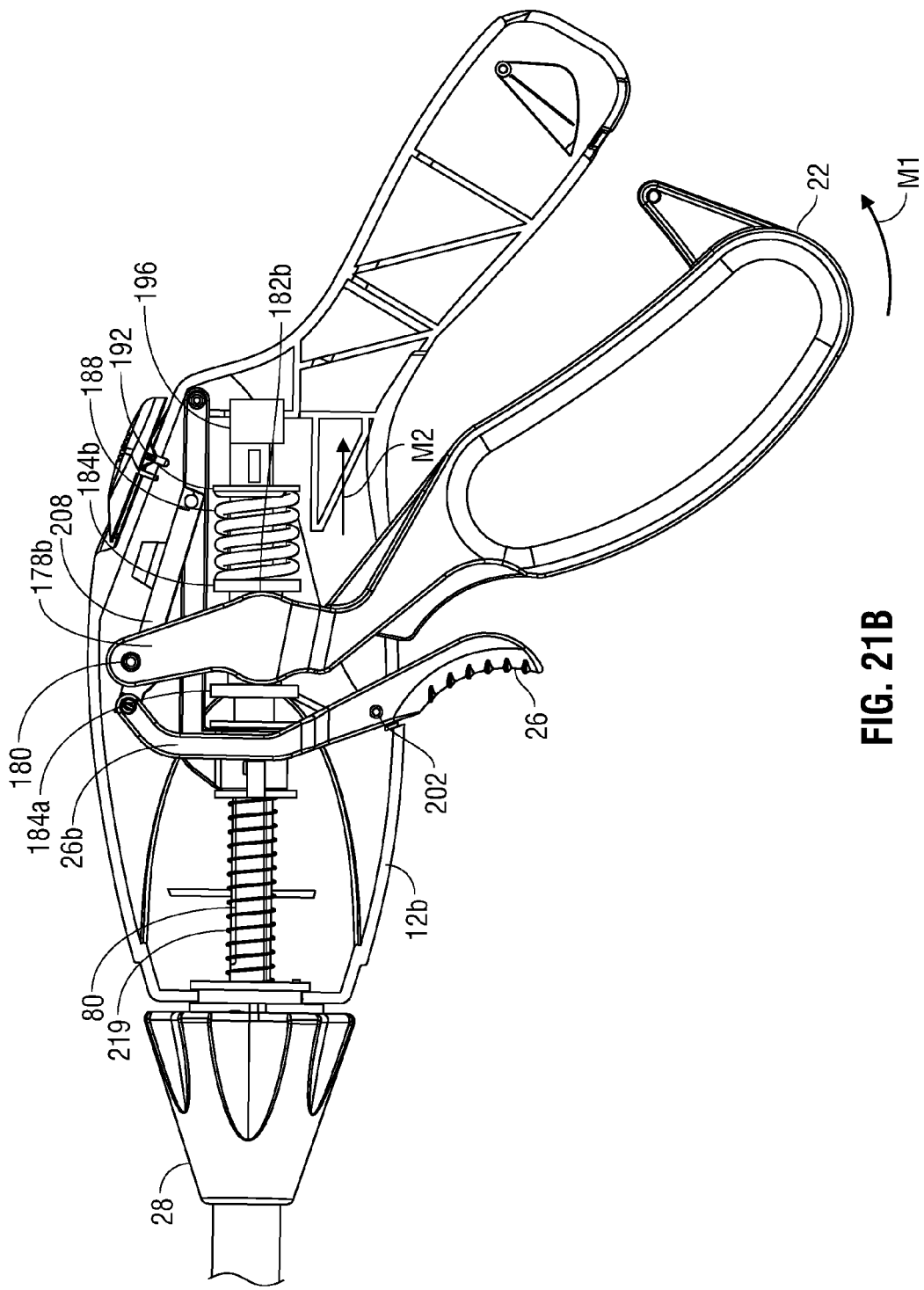
FIG. 21B is a side view of the proximal portion of the instrument of FIG. 17 depicting the movable handle in an intermediate position with respect to the stationary handle, which corresponds to a first closed configuration of the end effector wherein the jaw members encounter one another.
Figure 21C:
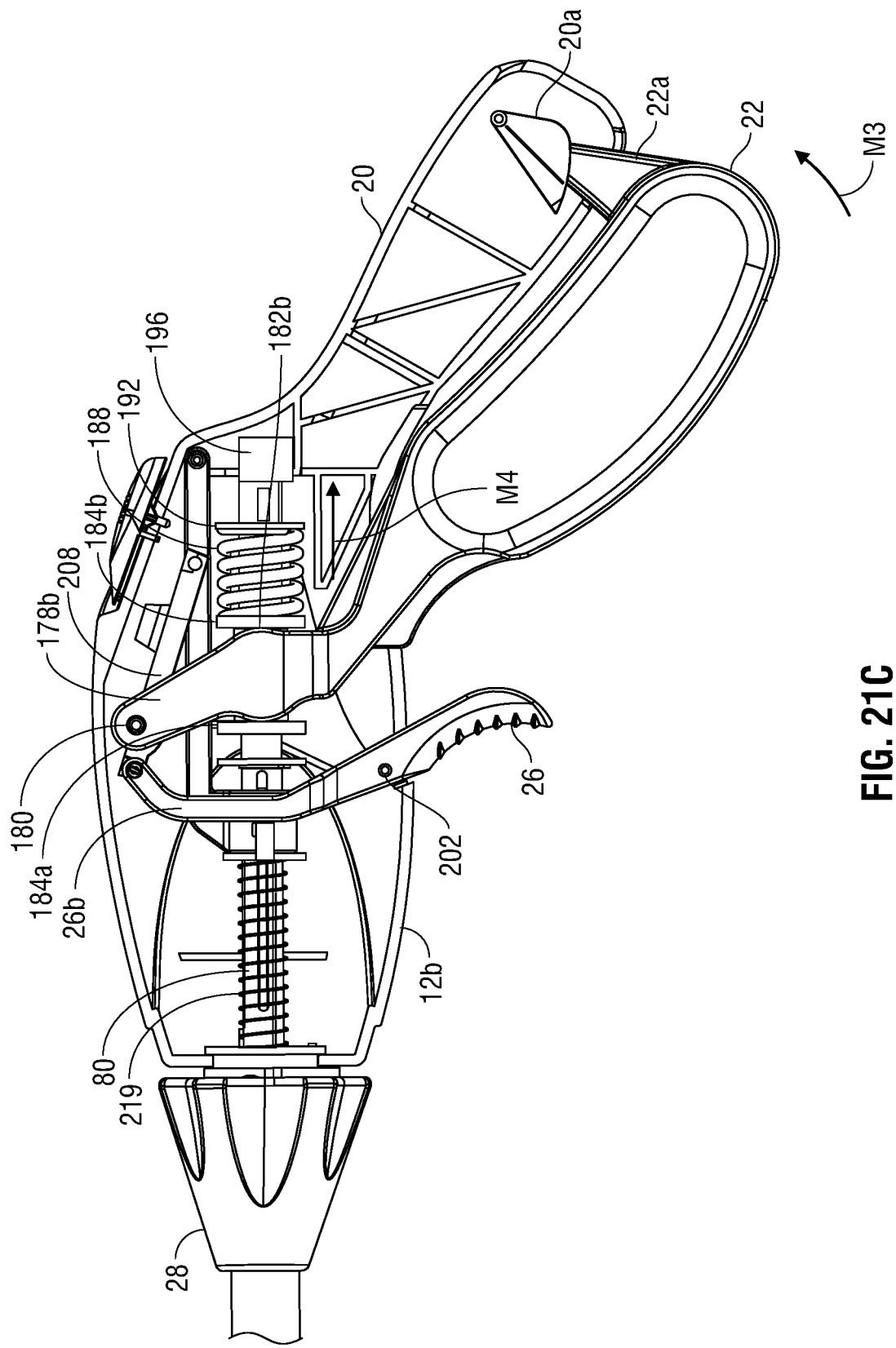
FIG. 21C is a side view of the proximal portion of the instrument of FIG. 17 depicting the movable handle in an approximated configuration with respect to the stationary handle, which corresponds to a second closed configuration of the end effector wherein the jaw members apply an appropriate pressure to generate a tissue seal.

The movable handle 22 may be moved from the intermediate position of FIG. 21B to the actuated or proximal position of FIG. 21C to increase the pressure applied by the jaw members. 30, 32. As the movable handle 22 pivots further about the pivot boss 180 in the direction of arrow M3, the drive surface 182b presses the proximal rim 184b of the drive collar 184 further distally against the spring 188 in the direction of arrow M4. The spring 188 is compressed against the spring keeper 192, and a tensile force is transmitted through the jaw drive rod 80 to the jaw members 30, 32. The tensile force supplied by the spring 188 ensures that the jaw members 30, 32 apply an appropriate pressure to effect a tissue seal. When the movable handle 22 is in the actuated or proximal position, electrosurgical energy may be selectively supplied to the end effector 14 to generate a tissue seal.

When the movable handle 22 is in the actuated or proximal position, a flange 22a on the moveable handle 22 is received in a railway 20a supported within the stationary handle 20. The railway 20a serves to temporarily lock the movable handle 22 in the proximal position against the bias of the spring 188, which biases the movable handle 22 from the proximal position of FIG. 21C to the intermediate position of FIG. 21B. Thus, the railway 20a permits the maintenance of pressure at the end effector 14 without actively maintaining pressure on the movable handle 22. The flange 22a may be released from the railway 20a by pivoting the movable handle 22 proximally and releasing the movable handle 22 to move under the influence of the spring 188. Operation of the railway 20a is described in greater detail in U.S. patent application Ser. No. 11/595,194 to Hixon et al., now U.S. Pat. No. 7,766,910. In some embodiments (not shown), the flange 22a and the railway 22a may be eliminated to provide an instrument without the temporary locking capability provided by these features.

Figure 21D:
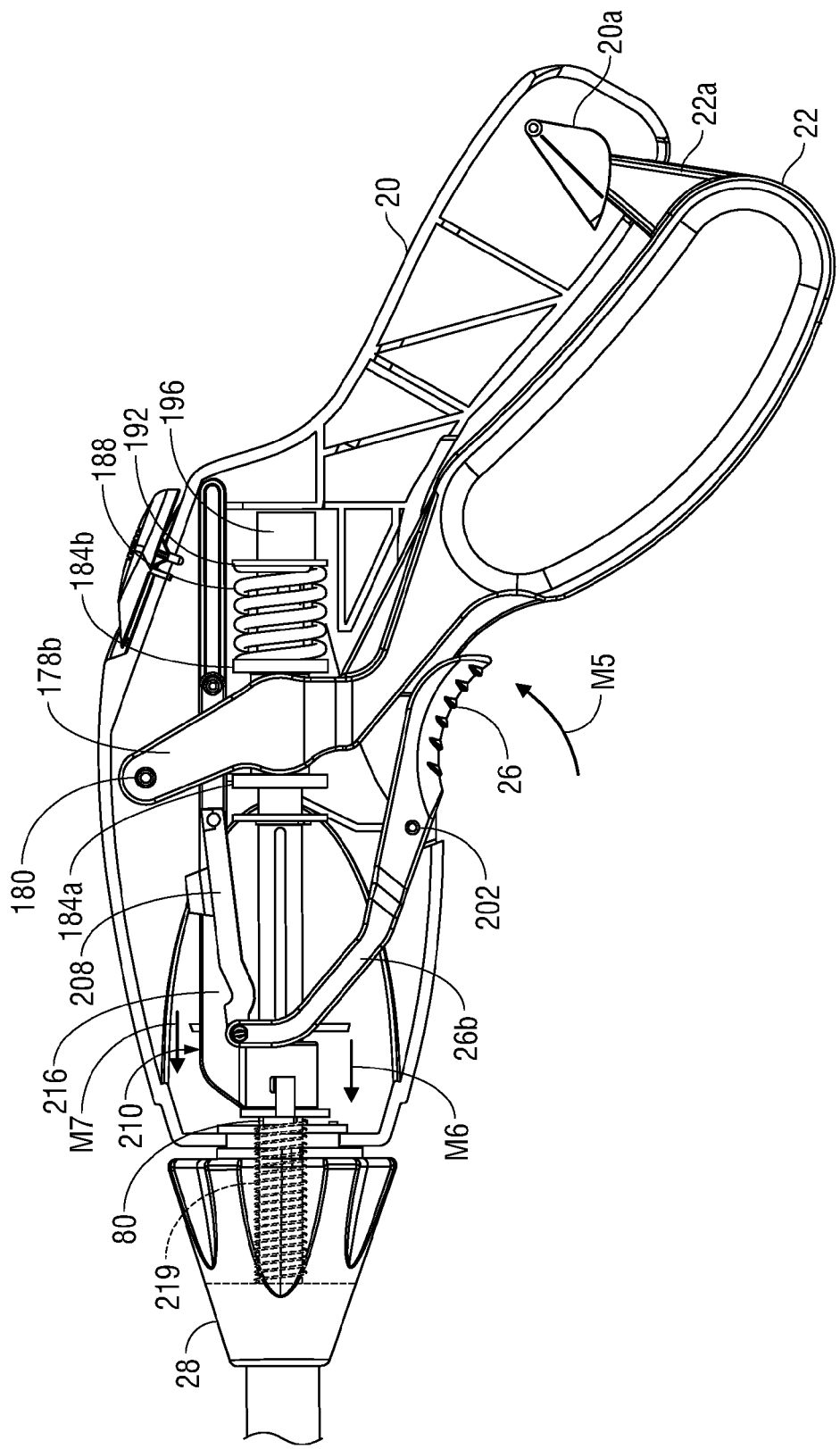
FIG. 21D is a side view of the proximal portion of the instrument of FIG. 17 depicting the knife trigger in an actuated configuration, which corresponds to an actuated or distal position of the knife with respect to the jaw members.

When the movable handle 22 is in the actuated or proximal position, the knife trigger 26 may be selectively moved from the distal position of FIG. 21C to the proximal position of FIG. 21D to advance the knife blade 56 distally through the jaw members 30, 32. The knife trigger 26 may be pivoted in the direction of arrow M5, about pivot boss 202 to advance the flange 26b of the knife trigger 26 distally in the direction of arrow M6. Movement of the flange 26b induces the link 208 to pivot with respect to the flange 26b of the trigger 26, and with respect to the knife arm 216 such that the link 208 draws the knife carriage 210 distally in the direction of arrow M7. As described above with reference to FIGS. 11 and 19-20, distal movement of the knife carriage 210 advances the knife blade 56 distally through the jaw members 30, 32.

Figure 22:
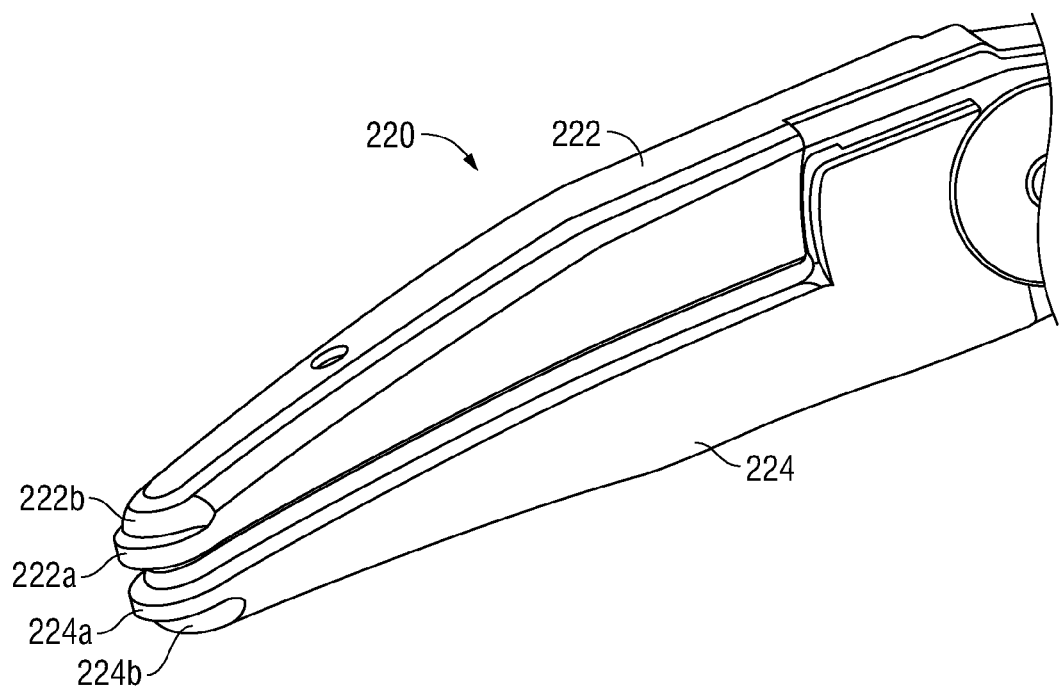
FIG. 22 is a perspective view of an alternate embodiment of an end effector including upper and lower jaw members with scalloped distal ends.

Referring now to FIGS. 22-29, various alternate components are described, which may be substituted individually or in combination for the similarly named components described above in order to provide specific functionality to a surgical instrument. With reference to FIG. 22, an alternate embodiment of an end effector 220 includes upper and lower jaw members 222 and 224 respectively, which are configured to facilitate blunt dissection of tissue. Each jaw member 222, 224 exhibits a scalloped distal end with a ledge 222a, 224a protruding distally from a less prominent portion 222b, 224b of the distal tip. When the end effector 220 is in the closed configuration as depicted, the ledges 222a, 224a may be pressed into tissue to be dissected. The end effector 220 may then be moved to the open configuration to separate the jaw members 222, 224 and any tissue gripped by the ledges 222a, 224a.

Figure 23:
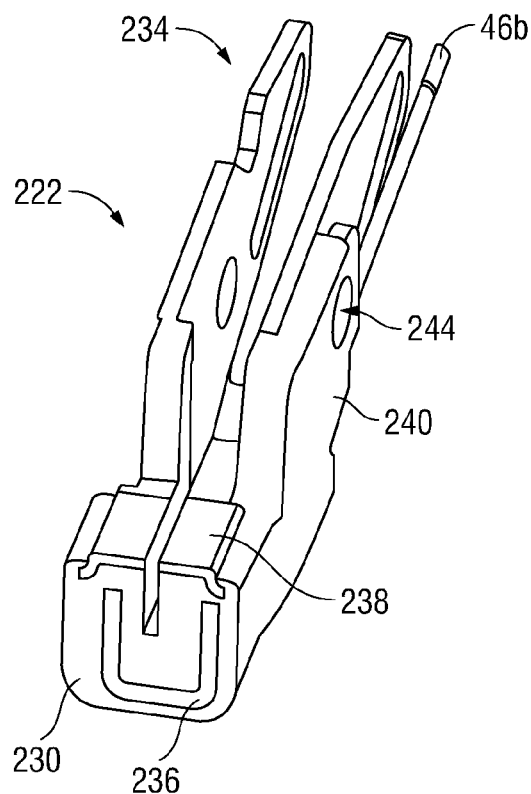
FIG. 23 is a cross-sectional, perspective view of an alternate embodiment of the lower jaw member of the end effector of FIG. 22.

The ledges 222a, 224a may be constructed of an electrically isolative material, e.g., the insulator 230 as depicted in FIG. 23. The upper jaw member 222 is constructed of three major components including a double-flag jaw insert 234, the insulator 230 and a sealing plate 238. The insulator 230 may molded onto a u-shaped channel 236 of the of the double-flag jaw insert 234 and the sealing plate 238 in a single-shot molding operation. The insulator 230 may completely surround the u-shaped channel 236, and may include various features such as the ledge 224a (FIG. 22) at the distal end thereof, and a wire guide 240 at a proximal end thereof.

Figure 24:
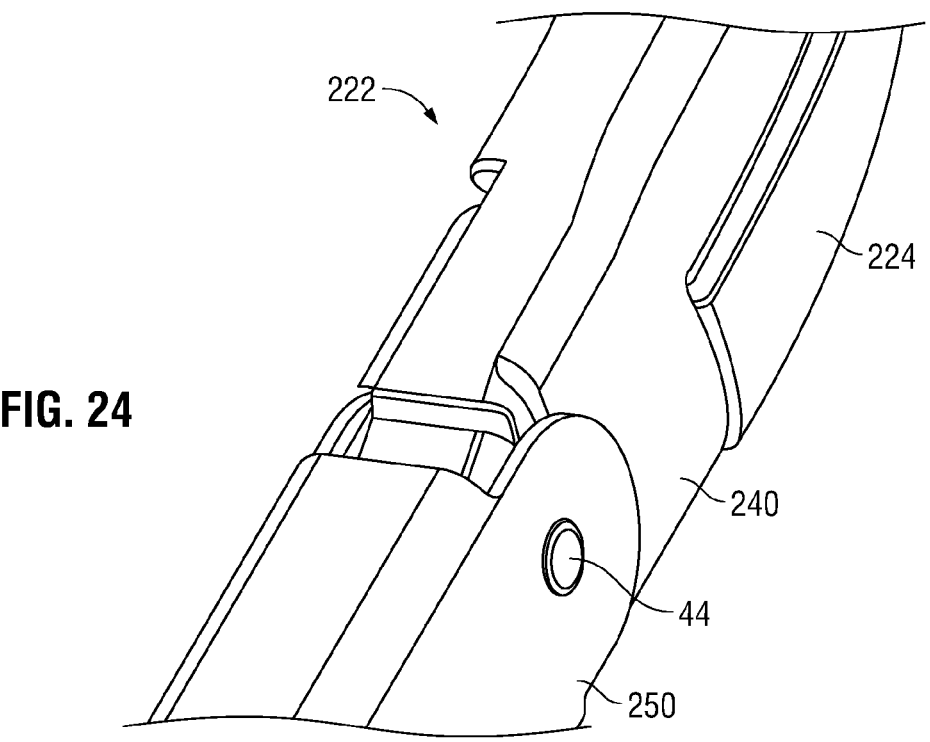
FIG. 24 is a perspective view of the end effector of FIG. 22 coupled to an outer shaft member, illustrating a wire guide incorporated into a proximal portion of the upper and lower jaw members.

The wire guide 240 is a portion of the insulator 230 that is molded to a lateral side of the double-flag jaw insert 234, and over the wire 46b that couples the sealing plate 238 to the electrosurgical generator 40 (FIG. 1) as described above. The wire guide 240 includes a hole 244 to provide clearance for a pivot pin 44 (FIG. 24), and is disposed on a single lateral side of the upper jaw member 222. Lower jaw member 224 (FIG. 22) may include a similar wire guide (not shown), which may be positioned on the opposing lateral side when the upper and lower jaw members 222, 224 are assembled to an outer shaft member 250 in an "offset" arrangement as depicted in FIG. 24. The wire guide 240 may thus protect the wire 46b from abrasion from the outer shaft member 250 as the upper jaw member 222 pivots about pivot pin 44.

Figure 25:
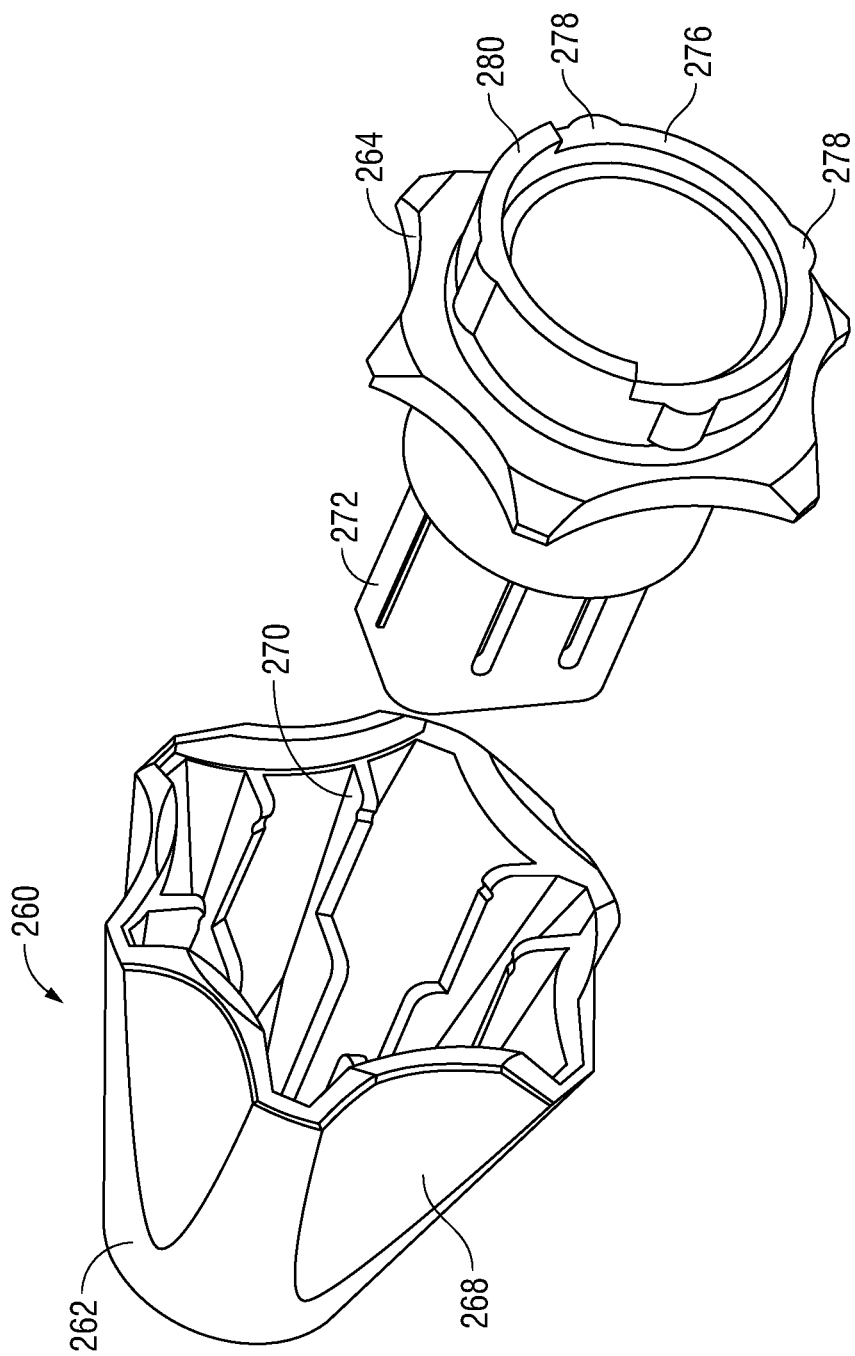
FIG. 25 is an exploded perspective view of an alternate embodiment of a rotation knob constructed of two distinct components.

Referring now to FIG. 25, a rotation knob 260 is constructed of two distinct components 262 and 264. An exterior component 262 provides gripping surfaces 268 which may be engaged by an operator in use. The exterior component 262 generally exhibits a thin wall construction to facilitate molding from a plastic or similar material. Inner wall portions 270 are provided to engage an inner component 264 of the rotation knob 260 in a snap-fit manner. The inner component 264 includes a distal engagement portion 272 for coupling the rotation knob 260 to the outer shaft member 250 (see FIG. 27), and a circular boss 276 extending proximally therefrom. The circular boss 276 includes radially spaced detents 278 projecting radially from an outer circumference thereof and a proximal extension 280 protruding longitudinally therefrom. The detents 278 and proximal extension 280 define the rotational limits of the rotation knob 260 as described below with reference to FIG. 28.

Figure 26:
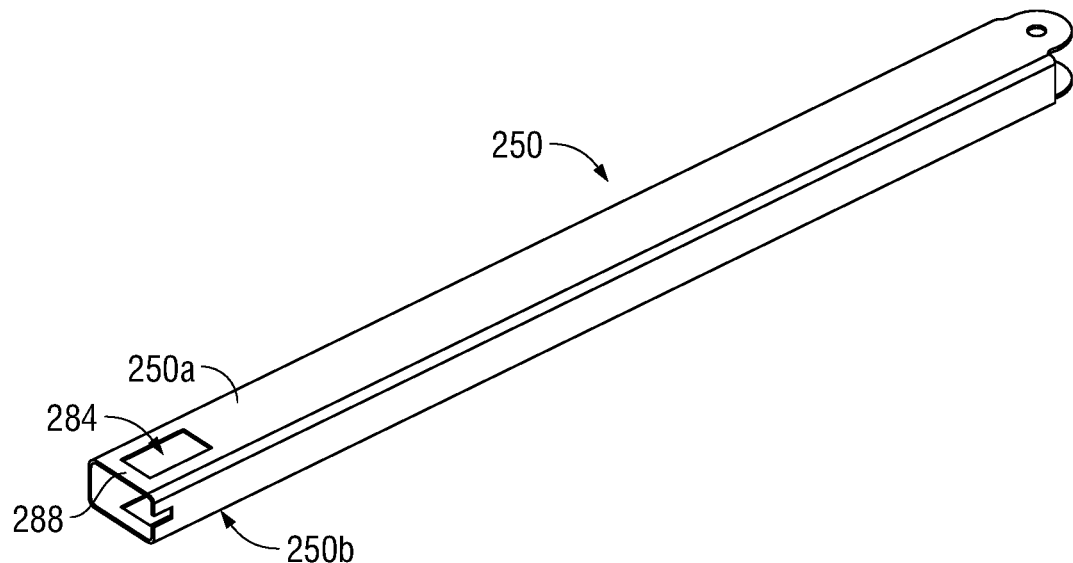
FIG. 26 is a perspective view of an alternate embodiment of an outer shaft member for connection with the rotation knob of FIG. 25.
Figure 27:
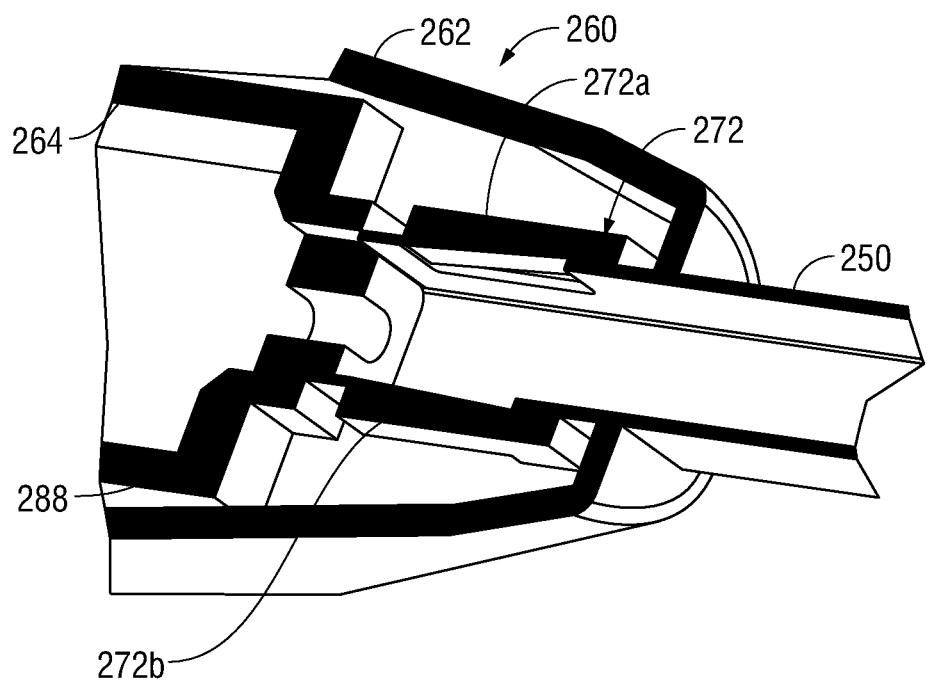
FIG. 27 is a cross-sectional, perspective view of the rotation knob of FIG. 25 assembled to the outer shaft member of FIG. 26.

Referring now to FIGS. 26 and 27, the outer shaft member 250 may be coupled to the rotation knob 260 in a snap-fit manner. The outer shaft member 250 includes a pair of rectangular openings 284 extending through vertical sidewalls 250a, 250b near a proximal end thereof. The rectangular openings 284 provide flexibility to the proximal end of the outer shaft member 250 such that a pair of latches 288 at a proximal end of the sidewalls 250a, 250b may be installed into the distal engagement portion 272 of the interior component 264 of the rotation knob 260. The distal engagement portion 272 includes tapered walls 272a, 272b to urge the latches 288 laterally inward temporarily as the outer shaft member 250 is inserted longitudinally between the walls 272a, 272b. Once the latches 288 have been inserted proximally beyond the walls 272a, 272b, the latches 288 will snap into place as the resiliency of the outer shaft member 250 urges the latches laterally outward. The outer shaft member 250 may thus be operatively coupled to the rotation knob 260.

Figure 28:
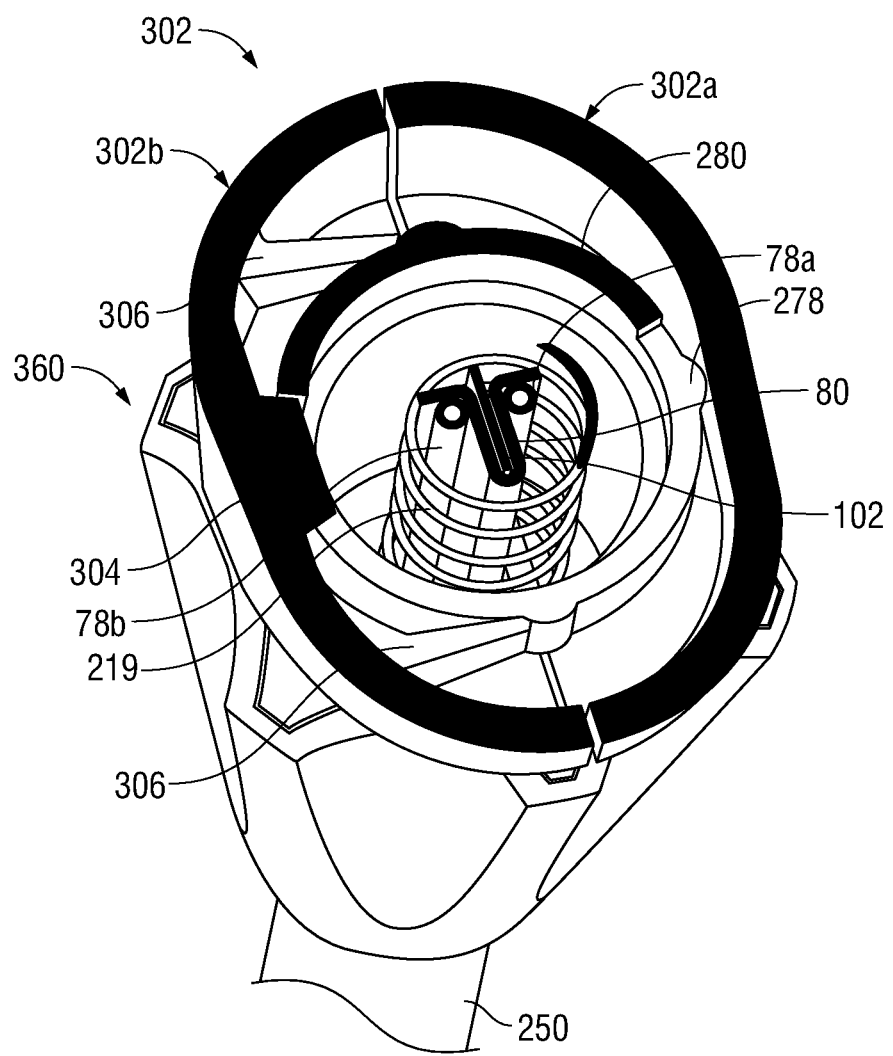
FIG. 28 is cross sectional, perspective view the rotation knob of FIG. 25 coupled to a alternate embodiment of a housing, illustrating stop features and detent arms for defining a "jaws up" configuration in addition to a jaws right and jaws left configuration.

Referring now to FIG. 28, the rotational motion of the rotation knob 260 is limited by its connection to a housing 302, which includes right and left housing halves 302a, 302b, respectively. A stop 304 projects laterally inward from housing half 302b and is positioned to engage the proximal extension 280 to prevent rotational motion of the rotation knob further than, in one embodiment, 180 degrees in either direction. A pair of the detents 278 extending from outer circumference of the rotation knob 260 engage a pair of cantilever arms 306 projecting from the housing half 302b. The engagement of the detents 278 with the cantilever arms 306 defines a relatively stable relation between the rotation knob 260 and the housing 302. In one embodiment, the detents 278 are radially spaced by about 90 degrees such that at least three relatively stable positions may be defined within the extent of the rotation permitted by proximal extension 280 and the stop 304. These positions may correspond to a configuration wherein jaw members 222 and 224 (FIG. 22) curve to the left, in an upward direction, and to right from the perspective of a user. The components for limiting the rotation of the rotation knob 260 are all defined on an interior of the housing 302, and thus, interference from foreign materials is limited.

The outer shaft member 250, rotation knob 260 and the housing 302 define a longitudinal passage through which jaw drive rod 80, knife 102 and wire conduits 78a and 78b may extend. The rotation knob 260 may also include an interior shelf (not shown) against which spring 219 may be compressed (see FIG. 21D for a depiction of the spring 219 in a compressed state).

Figure 29:
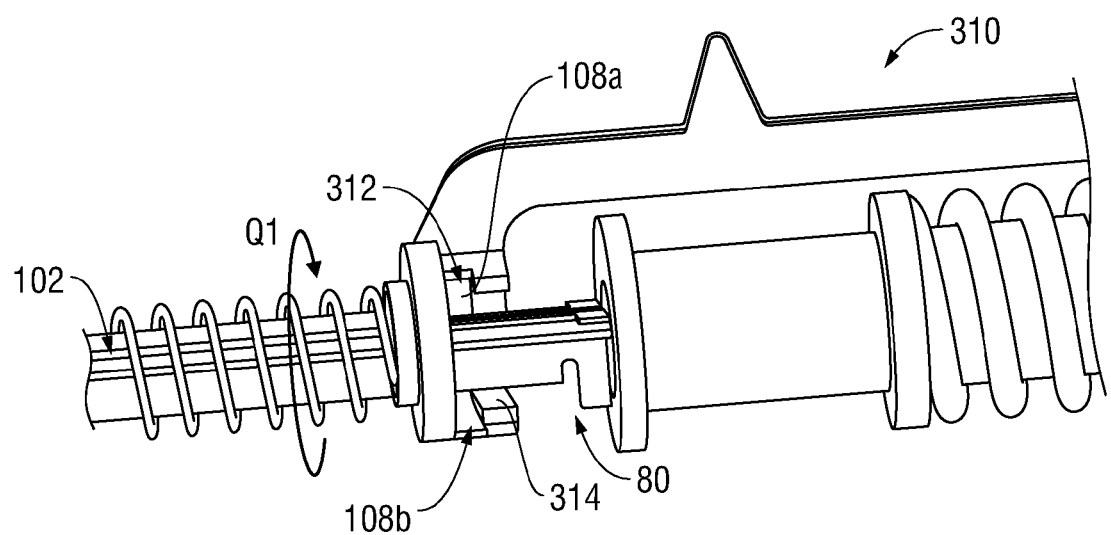
FIG. 29 is an alternate embodiment of a jaw drive mechanism including single-component a knife arm configured for connection to the knife of FIG. 3 without additional fasteners.

Referring now to FIG. 29, a knife carriage 310 may be operatively coupled to the knife 102 by relative rotation of the knife carriage 310 with respect to the knife. The knife carriage 310 includes a single component (compare with knife carriage 210 described above with reference to FIG. 19, which includes both a cap 218 and a sleeve 212 for capturing the knife 102). An opening 312 in the knife carriage 310 receives the proximal tabs 108a, 108b of the knife 102. Rotation of the knife carriage 310 in the direction of arrow Q1 captures the proximal tabs 108a, 108b against a proximal ledge of the knife carriage. Thus, longitudinal motion may be transmitted between the knife carriage 310 and the knife 102.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
a housing;
an elongated shaft coupled to the housing and defining a longitudinal axis;
a pair of opposing jaw members disposed at a distal portion of the elongated shaft, at least one of the pair of opposing jaw members including a cam slot; and
a drive rod having a generally u-shaped profile and configured to move longitudinally within the elongated shaft to translate a cam pin through the cam slot to move at least one of the jaw members relative to the other jaw member.

2. The surgical instrument according to claim 1, wherein a first jaw member of the pair of opposing jaw members includes a first pair of laterally spaced flanges and a second jaw member of the pair of opposing jaw members includes a second pair of laterally spaced flanges, the first and second pairs of flanges arranged in an offset configuration such that one flange of the pair of flanges of the first jaw member is positioned on a laterally exterior side of a corresponding flange of the pair of flanges of the second jaw member, and the other flange of the pair of flanges of the first jaw member is positioned on a laterally interior side of the other flange of the pair of flanges of the second jaw member.

3. The surgical instrument according to claim 2, wherein the drive rod is configured to move longitudinally through a laterally interior side of each of the flanges.

4. The surgical instrument according to claim 2, wherein each of the pairs of flanges extends proximally from a curved tissue engaging portion of each respective jaw member.

5. The surgical instrument according to claim 2, wherein the pair of opposing jaw members are pivotally coupled to the distal portion of the elongated shaft about a pivot axis.

6. The surgical instrument according to claim 5, wherein the pivot axis extends through each of the pairs of flanges transverse to the longitudinal axis defined by the elongated shaft.

7. The surgical instrument according to claim 2, wherein at least one of the flanges of the pair of flanges of each of the jaw members includes an electrically isolative wire guide disposed on a lateral side thereof and configured to receive an electrical wire.

8. The surgical instrument according to claim 7, wherein the wire guides are constructed of an electrically isolative plastic.

9. The surgical instrument according to claim 1, wherein the pair of opposing jaw members are disposed laterally offset relative to one another.

10. The surgical instrument according to claim 1, wherein the elongated shaft has a generally rectangular profile.

11. The surgical instrument according to claim 1, further comprising a knife configured to move longitudinally within the drive rod.

12. The surgical instrument according to claim 11, wherein the drive rod restricts lateral movement of the knife in a first lateral plane and a second lateral plane that is orthogonal to the first lateral plane.

13. The surgical instrument according to claim 11, wherein the drive rod includes an overfold such that the drive rod surrounds the knife on four lateral sides of the knife.

* * * * *